US011242526B2

(12) United States Patent
Ilyine et al.

(10) Patent No.: US 11,242,526 B2
(45) Date of Patent: Feb. 8, 2022

(54) PNA PROBE

(71) Applicant: Destina Genomica S.L., Granada (ES)

(72) Inventors: Hugh Alexander Ilyine, Haddington (GB); Juan J. Diaz-Mochon, Granada (ES); Salvatore Pernagallo, Granada (ES); Mavys Tabraue Chavez, Granada (ES); Mario Antonio Fara, Granada (ES)

(73) Assignee: Destina Genomica S.L., Granada (ES)

( * ) Notice: Subject to any disclaimer, the term of this patent is extended or adjusted under 35 U.S.C. 154(b) by 341 days.

(21) Appl. No.: 16/317,240

(22) PCT Filed: Jul. 12, 2017

(86) PCT No.: PCT/EP2017/067642
§ 371 (c)(1),
(2) Date: Jan. 11, 2019

(87) PCT Pub. No.: WO2018/011320
PCT Pub. Date: Jan. 18, 2018

(65) Prior Publication Data
US 2019/0233818 A1 Aug. 1, 2019

(30) Foreign Application Priority Data

Sep. 29, 2016 (GB) .................................. 1616556
Jul. 12, 2017 (ES) .............................. ES201630948

(51) Int. Cl.
*C07H 21/04* (2006.01)
*C12N 15/113* (2010.01)
*C12N 15/11* (2006.01)
*C12Q 1/68* (2018.01)
*C12Q 1/6816* (2018.01)

(52) U.S. Cl.
CPC .......... *C12N 15/113* (2013.01); *C12N 15/111* (2013.01); *C12Q 1/68* (2013.01); *C12Q 1/6816* (2013.01); *C12N 2310/3181* (2013.01)

(58) Field of Classification Search
None
See application file for complete search history.

(56) References Cited

U.S. PATENT DOCUMENTS

2017/0073748 A1* 3/2017 Lizardi ................ C12Q 1/6806

FOREIGN PATENT DOCUMENTS

WO 2009037473 3/2009
WO 2014169216 10/2014

OTHER PUBLICATIONS

Abed et al. "Reversible Binding of Gold Nanoparticles to Polymeric Solid Supports" Chemistry of Materials, 18:1247-1260 (2006).
Bialy et al. "Dde-protected PNA monomers, orthogonal to Fmoc, for the synthesis of PNA-peptide conjugates" Tetrahedron, 61(34):8295-8305 (2005).
Diaz-Mochon et al. "Full Orthogonality between Dde and Fmoc:? The Direct Synthesis of PNA-Peptide Conjugates" Organic Letters, 6(7): 1127-1129 (2004).
Dirksen et al. "Nucleophilic Catalysis of Hydrazone Formation and Transimination:? Implications for Dynamic Covalent Chemistry" Journal of the American Chemical Society, 128(49): 15602-15603 (2006).
Garg et al. "A ligand-free solid-supported system for Sonogashira couplings: applications in nucleoside chemistry" Chemical Communications, 36:4551-4553 (2005).
International Preliminary Report on Patentability corresponding to International Patent Application No. PCT/EP2017/067642 (7 pages) (dated Jan. 24, 2019).
Jang et al. "Peptide Nucleic Acid Array for Detection of Point Mutations in Hepatitis B Virus Associated with Antiviral Resistance" Journal of Clinical Microbiology, 48(9):3127-3131 (2010).
Li et al. "A photocleavable fluorescent nucleotide for DNA sequencing and analysis" Proceedings of the National Academy of Sciences, 100(2):414-419 (2003).
Maxam et al. "A new method for sequencing DNA" Proceedings of the National Academy of Sciences, 74(2):560-564 (1977).
Paulasova et al. "The peptide nucleic acids (PNAs): a new generation of probes for genetic and cytogenetic analyses" Annales de Génétique, 47:349-358 (2004).
Polyakov et al. "Imine exchange in O-aryl and O-alkyl oximes as a base reaction for aqueous 'dynamic' combinatorial libraries: A kinetic and thermodynamic study" Journal of Physical Organic Chemistry, 12:357-363 (1999).
Portal et al. "High Throughput Physical Organic Chemistry: Analytical Constructs for Monomer Reactivity Profiling" Journal of Combinatorial Chemistry, 7(4):554-560 (2005).
Sanger et al. "DNA sequencing with chain-terminating inhibitors" Proceedings of the National Academy of Sciences, 74(12):5463-5467 (1977).
Seo et al. "Photocleavable fluorescent nucleotides for DNA sequencing on a chip constructed by site-specific coupling chemistry" Proceedings of the National Academy of Sciences, 101(15):5488-5493 (2004).
Shi et al. "A review: Fabrications, detections and applications of peptide nucleic acids (PNAs) microarray" Biosensors and Bioelectronics, 66:481-489 (2015).
Thoresen et al. "Rigid, Conjugated, Fluoresceinated Thymidine Triphosphates: Syntheses and Polymerase Mediated Incorporation into DNA Analogues" Chemistry: A European Journal, 9(19)14603-4610 (2003).
Worthington et al. "Mixed-sequence pyrrolidine-amide oligonucleotide mimics: Boc(Z) synthesis and DNA/RNA binding properties" Organic & Biomolecular Chemistry, 5:249-259 (2007).

(Continued)

*Primary Examiner* — Kimberly Chong
(74) *Attorney, Agent, or Firm* — Myers Bigel, P.A.

(57) ABSTRACT

Disclosed herein are improved PNA based monomers, nucleobases, oligomers and probes for use in a variety of different methods of analysing nucleic acids. Further, the disclosure provides methods of preparing the modified and improved PNA molecules as well as methods of using the same.

10 Claims, 19 Drawing Sheets

Specification includes a Sequence Listing.

(56) References Cited

OTHER PUBLICATIONS

Vaillancourt et al. "Synthesis and Biological Activity of Aminoguanidine and Diaminoguanidine Analogues of the Antidiabetic/Antiobesity Agent 3-Guanidinopropionic Acid" Journal of Medicinal Chemistry, 44:1231-1248 (2001).

International Search Report and the Written Opinion of the International Searching Authority corresponding to International Patent Application No. PCT/EP2017/067642 (14 pages) (dated Oct. 16, 2017).

Menchise et al. "Insights into peptide nucleic acid (PNA) structural features: The crystal structure of a D-lysine-based chiral PNA-DNA duplex" Proceedings of the National Academy of Sciences, 100(21):12021-12026 (2003).

Sforza et al. "Fast, Solid-Phase Synthesis of Chiral Peptide Nucleic Acids with a High Optical Purity by a Submonomeric Strategy" European Journal of Organic Chemistry, 2003(6):1056-1063 (2003).

Sugiyama et al. "Chiral Peptide Nucleic Acids with a Substituent in the N-(2-Aminoethy)glycine Backbone" Molecules, 18:287-310 (2013).

Tankevich et al. "Structure/activity relationships of negatively charged peptide nucleic acid oligomers" FEBS Journal, 282(Suppl. 1):347 (2015).

Huang et al. "Synthesis of Enantiopure gamma-Glutamic Acid Functionalized Peptide Nucleic Acid Monomers" Bulletin of the Korean Chemical Society, 31(7):2054-2056 (2010).

Kleiner et al. "DNA-Templated Polymerization of Side-Chain-Functionalized Peptide Nucleic Acid Aldehydes" Journal of the American Chemical Society, 130(14):4646-4659 (2008).

Niu et al. "Gamma-AApeptides: design, synthesis and evaluation" New Journal of Chemistry, 35(3):542-545 (2011).

Search Report under Section 17 corresponding to GB Application No. GB1616556.5 (2 pages) (dated Aug. 4, 2017).

Tilanl et al. "Evaluating the Effect of Ionic Strength on Duplex Stability for PNA Having Negatively or Positively Charged Side Chains" PLoS ONE, 8(3):e58670 (2013).

Vieville et al. "Duplex formation and secondary structure of gamma-PNA observed by NMR and CD" Biophysical Chemistry, 210:9-13 (2016).

\* cited by examiner

| Spotted probes 50uM | DestiNA reaction C-BIOT | |
|---|---|---|
| | KWT | K12S |
| | 2014-12-18_4 | 2014-12-18_6 |
| Control | 100 | 100 |
| 12SRC_18U | 37 | 7 |
| 12SRC_CBC | 43 | 3 |
| 12SRC_CBU | 41 | 6 |
| 12DAV_18UG | 29 | 5 |
| 12DAV_18U | 25 | 4 |
| 12DAV_CBC | 33 | 5 |
| 12DAV_CBU | 26 | 5 |
| 13SRC_18UG | 44 | 4 |
| 13SRC_18U | 42 | 7 |
| 13SRC_CBC | 43 | 2 |
| 13DAV_18UG | 26 | 4 |
| 13DAV_18U | 23 | 5 |
| 13DAV_CBC | 30 | 2 |

Figure 6

|  | KWT | K12S |
|---|---|---|
| K12SRC 3RCC | 71 | 5 |
| K13SRC 3RCC | 77 | 9 |
| K12DAV 3RCC | 66 | 8 |
| K13DAV 3RCC | 67 | 11 |

Figure 9

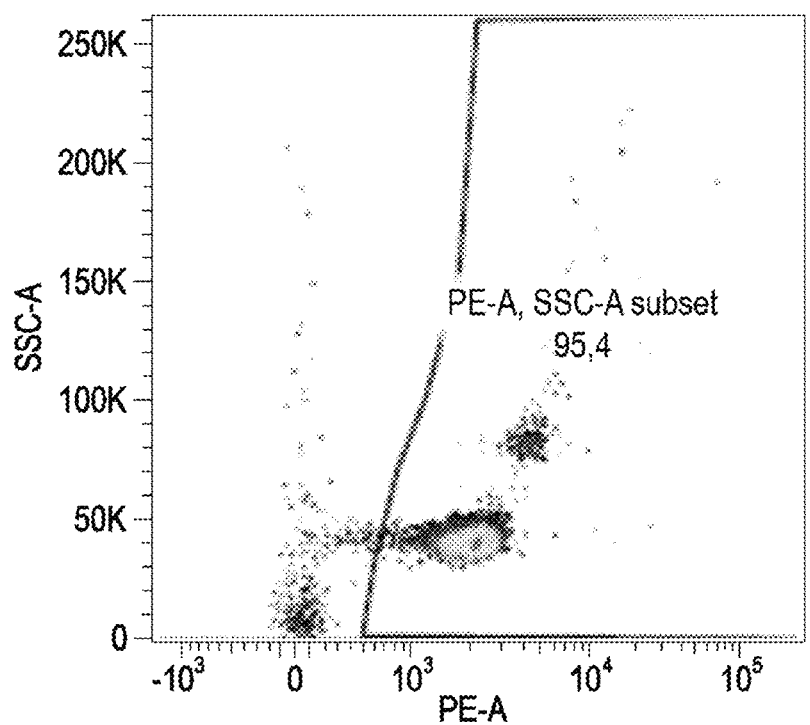
DGL21_6.0 Positive
control with Oligo DNA21
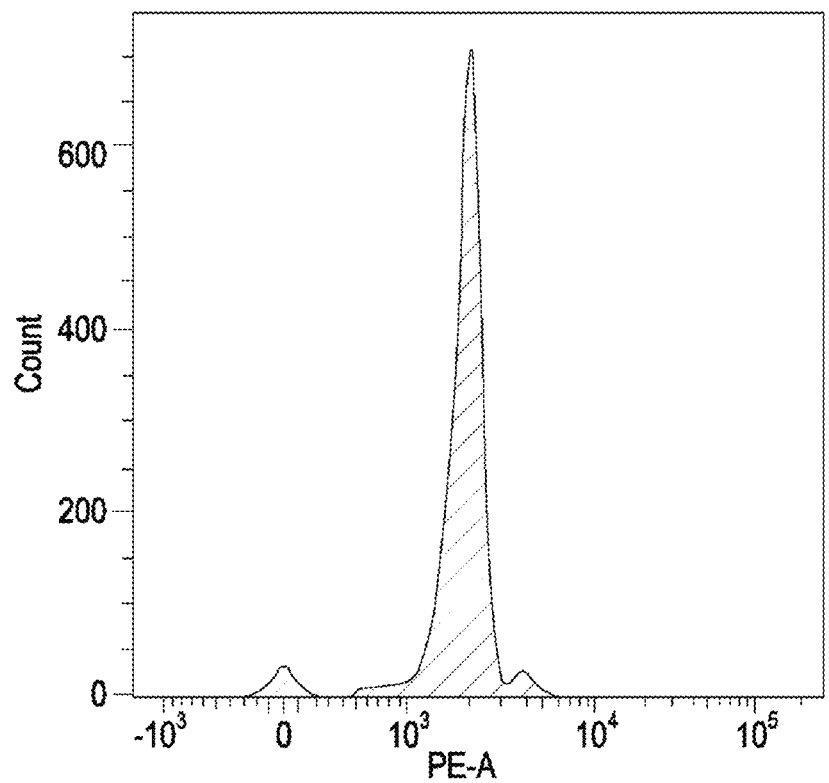
Figure 14

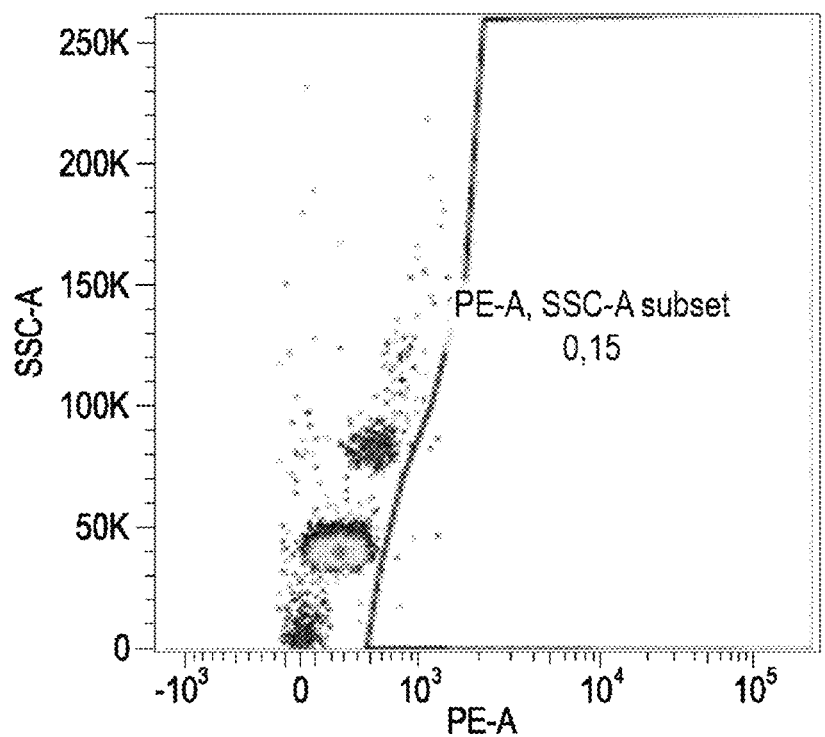
DGL21_6.0 control
with water
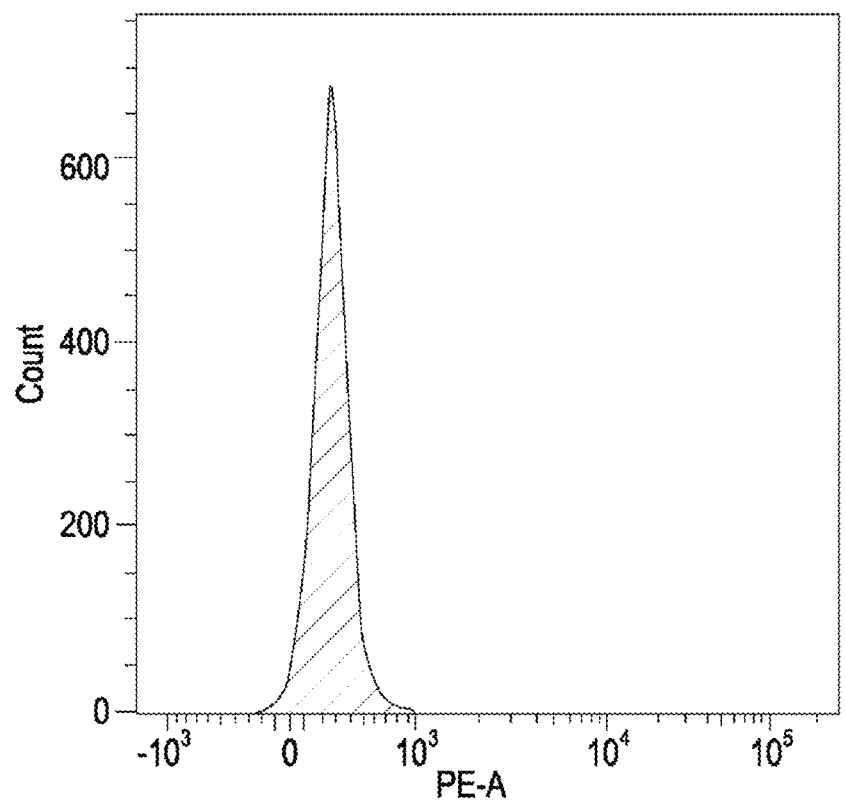
Figure 14 continued

A.
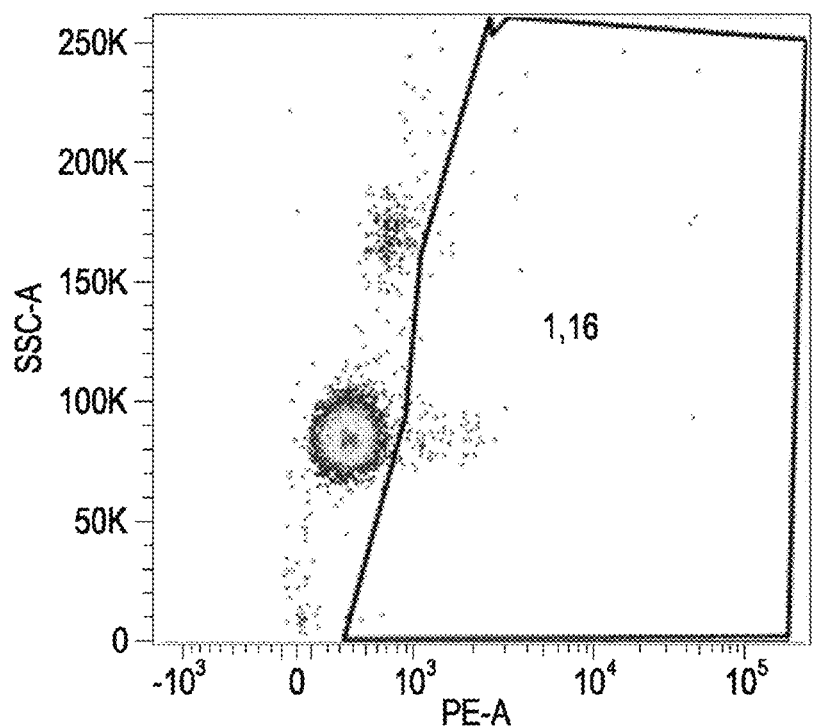
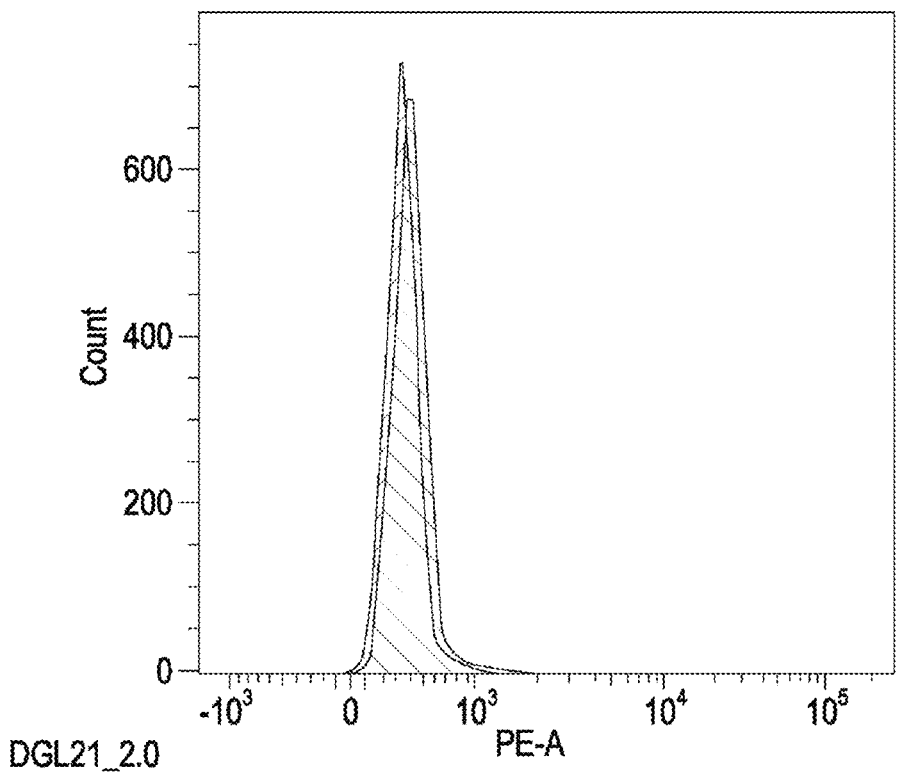
Figure 15

B.
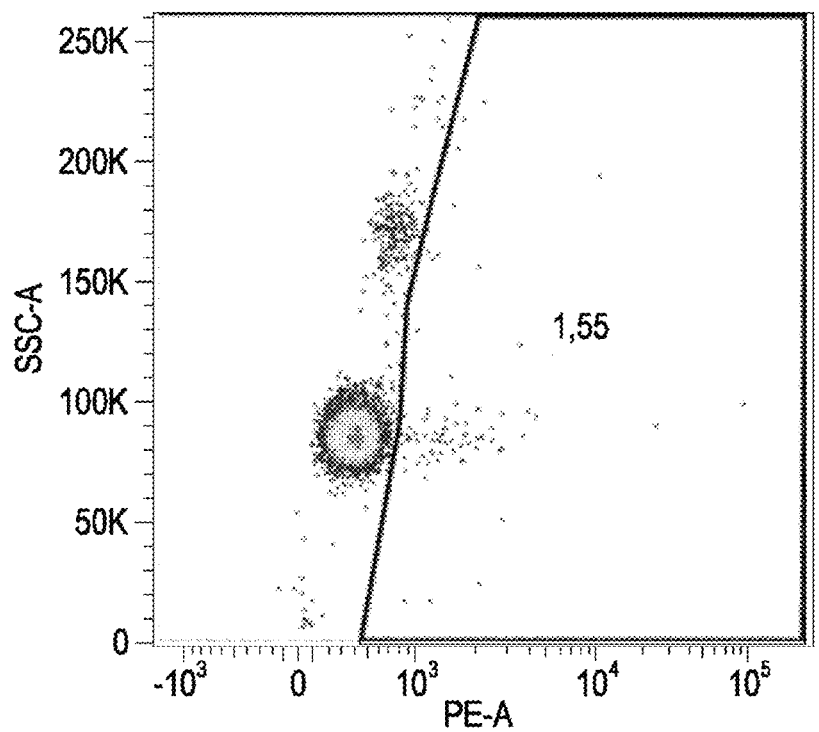
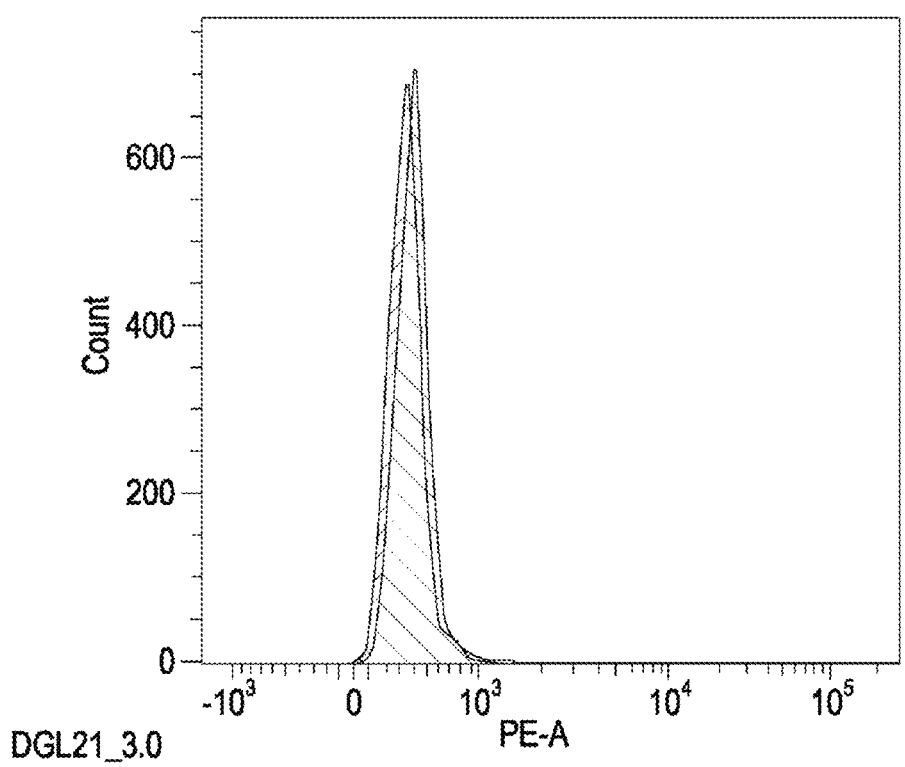
Figure 15 continued

| CODE | COMPLEMENTARY DGLs TO 22MER HSA-miR122-5p | N-TERM TO C-TERM | SIZE |
|---|---|---|---|
| DGL122_1.2 | >HSA-miR-122-5p MIMAT0000421 UGGAGUGUGACAAUGGUGUUUG (SEQ ID NO:17) | AACA—ATTGTCACTC (SEQ ID NO:18) | 18 MER |
| DGL122_3.0 | >HSA-miR-122-5p MIMAT0000421 UGGAGUGUGACAAUGGUGUUUG (SEQ ID NO:17) | CAAACA—CATTGTCACA (SEQ ID NO:19) | 17 MER |
| DGL122_5.0 | >HSA-miR-122-5p MIMAT0000421 UGGAGUGUGACAAUGGUGUUUG (SEQ ID NO:17) | ACCATTGTCA—ACTCCA (SEQ ID NO:20) | 17 MER |
| DGL122_4.0 | >HSA-miR-122-5p MIMAT0000421 UGGAGUGUGACAAUGGUGUUUG (SEQ ID NO:17) | CACCATTGT—ACACTCCA (SEQ ID NO:21) | 18 MER |
| DGL122_4.1 | >HSA-miR-122-5p MIMAT0000421 UGGAGUGUGACAAUGGUGUUUG (SEQ ID NO:17) | CACCATTGT—ACACTCCA (SEQ ID NO:22) | 18 MER |
| DGL122_4.2 | >HSA-miR-122-5p MIMAT0000421 UGGAGUGUGACAAUGGUGUUUG (SEQ ID NO:17) | CACCATTGT—ACACTCCA (SEQ ID NO:23) | 18 MER |

Figure 16

| CODE | COMPLEMENTARY DGLs TO 22MER HSA-miR21-5p | N-TERM TO C-TERM | SIZE |
|---|---|---|---|
| DGL21_2.0 | >HSA-miR-21-5p MIMAT0000076 UAGCUUAUCAGACUGAUGUUGA (SEQ ID NO:27) | T-C-A-A-C-A-T-C-G-T-C-T-C-A-G-A-T-A (SEQ ID NO:24) | 17 MER |
| DGL21_3.0 | >HSA-miR-21-5p MIMAT0000076 UAGCUUAUCAGACUGAUGUUGA (SEQ ID NO:27) | A-T-C-A-G-T-C-T-G-T-A-A-G-C-T-A (SEQ ID NO:25) | 17 MER |
| DGL21_6.0 | >HSA-miR-21-5p MIMAT0000076 UAGCUUAUCAGACUGAUGUUGA (SEQ ID NO:27) | C-A-A-C-A-T-C-G-T-C-T-G-A-T-A-A-G-C (SEQ ID NO:26) | 19 MER |

Figure 17

PNA PROBE

FIELD OF THE INVENTION

The present invention relates to peptide nucleic acid compounds. In particular, though not exclusively, the present invention relates to peptide nucleic acid monomers, dimers, and/or oligomers, modified to incorporate a moiety such as a charged moiety at a desired location, e.g., in the backbone thereof.

BACKGROUND TO THE INVENTION

DNA sequencing is a known procedure that has been the subject of much research. Various methods of DNA sequencing have been reported, including the chemical approach of Maxim and Gilbert (A. M. Maxam and W. Gilbert, *PNAS*, 1977, 74, 560-564) and the enzyme based methods of Sanger (F. Sanger et al., *PNAS*, 1976, 5463-5467).

A number of newer approaches have been reported, which fall into three categories: (i). Sequencing by repetitive single base addition, (ii) Pyrosequencing and (iii) Restriction enzyme mediated cleavage or kinase ligation with deconvolution/decoding.

Examples of such methods are disclosed in PCT Application Publication No. VO 2009/037473 (Bradley et al.).

Peptide nucleic acids (PNA) are synthetic compounds which have been used in a number of applications, including as genetic probes (see review by P. Paulosova and F. Pellestor, *Ann. Genetique*, 2004, 47, 349-358).

Peptide nucleic acid (PNA) is similar to the naturally occurring nucleic acids—deoxyribonucleic acid (DNA) and ribonucleic acid (RNA). However, While DNA and RNA possess a deoxyribose or ribose sugar backbone respectively, the backbone of PNA comprises repeating N-(2-aminoethyl)-glycine units which are linked by peptide bonds. The various pyrimidine and/or purine bases (or nucleobases) of PNA, are linked to the peptide backbone by amide bond formation. One of skill in the art will understand that a single nucleobase linked via an amide bond to a single N-(2-aminoethyl)-glycine unit may be described as a PNA monomer, but other PNAs may include, for example, those containing modified aminoethyl-glycine backbones, such as, for example, pyrrolidine-based (R. J. Worthington et al. *Org. Biomol. Chem.*, 2007, 5, 249-259) and indole-based DNA mimics (Formula 9). One skilled in the art will recognise other suitable oligomers.

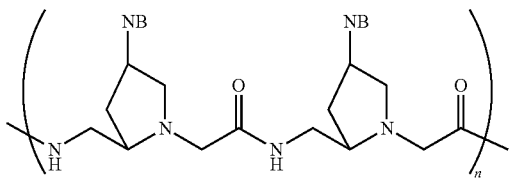

Formula 9

An example of the use of a PNA array for detection of point mutations in antivial-resistant Hepatitis B virus is discussed in Hyunjung Jang et al., *Journal of Clinical Microbiology*, 2010, Vol. 48, No. 9, 3127-3131.

A review of fabrications, detections and applications of peptide nucleic acids (PNAs) microarrays is discussed in Huanhuan Shi et al., *Biosensors and Bioelectronics*, 2015, 66, 481-489.

PCT Application Publication No. WO 2009/037473 (Bradley et al.) discloses modified nucleobases, and modified PNA monomers and dimers and oligomers thereof, as well as their use in genetic analysis methods such as sequencing nucleic acids and characterising Single Nucleotide Polymorphisms (SNP). SNP represents a form of variation in a genome wherein a particular nucleotide of the genome varies between members of a population. By way of example, a SNP may comprise two alleles (i.e. one of two possible nucleotides at a particular locus)—and, in such cases, some of the individuals within a population may carry one SNP allele at a particular locus while others may carry the other allele at the same locus.

WO 2009/037473 (Bradley et al.) discloses a PNA oligomer in which one or more of the secondary amines of the peptide backbone are not derivatised to comprise a nucleobase and are left uncoupled. The provision of such "blank" or "abasic" PNA unit provides for improved characterisation of a nucleobase in a nucleic acid sequence. For example, such method may comprise contacting a nucleic acid with the modified peptide nucleic acid (PNA) oligomer capable of hybridising to a portion of the nucleic acid and lacking a nucleobase complementary to a nucleobase of the nucleic acid, to form a nucleic acid/PNA duplex; and contacting the nucleic acid/PNA duplex with modified bases comprising a detectable tag. The modified nucleobase complementary to the nucleobase of the nucleic acid integrates with the nucleic acid/PNA duplex, and can then be characterised by means of the detectable tag.

However, it has been observed that the provision of one or more "blank" or "abasic" units in a PNA oligomer probe may lead to unexpected difficulties. For example, when the probe is attached to the surface of a solid support, e.g. a resin support material, it was observed that the space created by the absence of a nucleobase in the "blank" position, can cause the probe to flex, bend or otherwise deform from its "normal" linear configuration. This may lead to a number of problems:

Firstly, it was found that such probes can have a tendency to bind not only with nucleobases complementary to the nucleobase of the nucleic acid to be characterised, but also with nucleobases which are not complementary to the nucleobase to be characterised. This phenomenon may be described as reduced specificity.

Secondly, it was found that the efficacy or yield of detection of probes bound with nucleobases complementary to the nucleobase of the nucleic acid to be characterised, e.g., by detection of a detectable tag associated with the modified nucleobase incorporated in the "blank" position of the PNA probe, can vary and/or can be affected and/or reduced. This phenomenon may be described as reduced sensitivity.

The object of the present invention is to obviate or mitigate at least one of the aforementioned problems associated with the prior art.

SUMMARY OF THE INVENTION

The present invention is based on the finding that PNAs modified to include a charged moiety or a moiety capable of carrying a charge at a predetermined pH may be used to provide PNA molecules which hybridise complementary nucleic acid strands better as compared to PNA molecules prepared using PNA monomers not modified in this way.

The modifications described herein may be applied to any type of PNA based molecule including, for example PNA monomers, dimers, oligomers and PNA based probes (for convenience, these PNA based molecules shall hereinafter be collectively referred to as "PNA molecules").

One of skill will appreciate that PNA molecules have numerous uses and may (in certain protocols) be immobilised to solid substrates—under such conditions, prior art PNA based molecules have been found to, in use, exhibit a degree of undesirable deformation, flexing and/or bending. The undesirable deformation, flexing and/or bending may affect the performance (e.g., specificity and/or sensitivity) of the PNA molecule in an assay—preventing proper target binding and the like.

The inventors have discovered that by modifying PNA monomers to include a charged moiety or a moiety capable of carrying a charge at a predetermined pH, it is possible to improve the stability of PNA molecules such that, for example, in use, the PNA molecule more readily retains its conformation, exhibits less (or no significant or substantial) deformation, flexing and/or bending—particularly when immobilised to a surface or substrate; PNA molecules prepared from any of the modified PNAs described herein may also exhibit improved performance in assays including genetic analysis and nucleobase characterisation assays.

According to a first aspect of the invention, there is provided a PNA monomer comprising at its gamma position a charged moiety or a moiety capable of carrying a charge at a predetermined pH.

The PNA monomer may be derived from a glycine unit.

Typically, the PNA monomer may be derived from a N-(2-aminoethyl)-glycine unit. As stated, the PNA monomer may comprise at the gamma position a charged moiety, or a moiety capable of carrying a charge at a predetermined pH.

The PNA monomer may have the general formula:

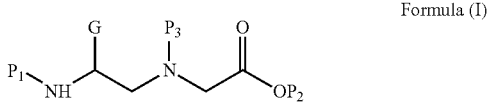

Formula (I)

wherein: G is a charged moiety, or a moiety capable of carrying a charge at a predetermined pH;
$P_1$ is a protective group P, or is hydrogen;
$P_2$ is a protective group P, or is hydrogen, or is a group selected from the list consisting of alkyl, cycloalkyl, aryl, aralkyl, or halogen,
$P_3$ is hydrogen, or is a protective group P, or is a group represented by formula (II) below:

Formula (II)

wherein NB is a nucleobase.

Throughout this specification, the term "comprising" is used to denote that aspects and embodiments of this disclosure "comprise" a particular feature or features. The term "comprising" may also encompass aspects and/or embodiments which "consist essentially of" or "consist of" the relevant feature or features.

Advantageously, the provision of a charged moiety, or a moiety capable of carrying a charge at a predetermined pH, at the gamma position of the PNA monomer, allows the preparation of a PNA molecule, e.g., a PNA oligomer, having a more stable configuration, particularly when the probe is attached to the surface of a solid support. Such a PNA oligomer, e.g, PNA probe, is less prone to flexing, bending or otherwise deforming from its "normal" linear configuration. For example, when the probe is used in genetic analysis methods such as methods for sequencing nucleic acids and characterising Single Nucleotide Polymorphisms (SNP), the modifications described herein may lead to probes having improved specificity and/or improved sensitivity towards a base complementary to the nucleobase of the nucleic acid to be characterised.

Without wishing to be bound by theory, it is suggested that the provision of a charged moiety, or a moiety capable of carrying a charge at a predetermined pH, at the gamma position of the PNA monomer, introduces a chiral centre in the PNA monomer.

In one embodiment, $P_3$ is not a group represented by formula (II). In such instance $P_3$ may be a protective group P or may be hydrogen.

A protective group ("P") will be understood as referring to a group capable of further derivatizing the group to which P is attached.

In some embodiments, the protective group P may be selected from the list consisting of acetyl, N-[1-(4,4-dimethyl-2,6-dioxocyclohex-1-ylidene)ethyl] (Dde), fluorenylmethoxycarbonyl (Fmoc), trityl groups, disulfide (Ardec (aryidithioethyloxycarbonyl)) light cleavage protecting group (nitroveratyl based), butyloxycarbonyl (Boc), benzyloxycarbonyl (Cbz), trifluoroacetyl (Tfa), phthalimide, benzyl, allyloxycarbonyl (Alloc), toluensulfonyl (Ts), methoxymethyl ether (MOM), tetrahydropyranyl ether (THP), allyl ether, butyl ether, benzylidene acetal (Green, Wiley-Interscience, New York, 1999).

One of skill in the art will appreciate that the term "nucleobases" (NB in formula II: otherwise known as or referred to herein as "nucleotides" or "bases") may comprise purines and pyrimidines. The term "nucleobase" may include, for example the specific bases adenine, guanine, thymine, cytosine and uracil as well as variants such as, for example, xanthine, hypoxanthine, isoguanine, uric acid and the group of nucleobases collectively known as the "synthetic bases".

When, in the compound of Formula (I), $P_3$ is a protective group P or is hydrogen, the secondary amine of the peptide monomer is not derivatised to comprise a nucleobase NB. In other words, the secondary amine of the PNA backbone is not derivatised to comprise a nucleobase and it is left "uncoupled". In such instances the PNA monomer may be described as a "blank" or "abasic" PNA monomer (the term "blank" referring to the underivatised secondary amine). The provision of such "blank" or "abasic" PNA monomer may be particularly useful in methods which facilitate the characterisation of a nucleobase in a nucleic acid sequence. Suitable methods are described, for example, in WO 2009/037473 (Bradley et al.: the entire contents of which are incorporated herein by reference). Typically, in such instance, $P_3$ may be a protective group P. By such provision, chemical reactions of the secondary amine of the pseudo-peptide monomer may be avoided and/or prevented.

Blank or abasic PNA monomers as described herein may be used to create PNA probes. A PNA probe may take the form of a PNA oligomer comprising a number of PNA monomers, including at least one PNA monomer which is a blank or abasic monomer. The PNA oligomer (probe) may be capable of hybridising to a specific nucleic acid sequence and though the inclusion of a blank/abasic PNA monomer, lacks a base complementary to that of a nucleotide to be characterised.

As stated, detailed methods which might exploit PNA probes (oligomers) of the type described herein are described in WO2009/037473 (incorporated herein by reference) and the present invention provides modified PNA molecules for use in these methods. These modified molecules exhibit greater or improved stability in, for example, genetic analysis methods including those nucleobase/SNP characterisation methods described in WO2009/037473.

The PNA molecules described herein may be used in combination with one or more "modified bases". The term "modified base" may be taken to encompass bases/nucleobases comprising an alkyl chain further comprising functional groups capable of reversible covalent reactions. Preferably, the heterocycle of the bases may be modified so as to comprise the alkyl chain and functional groups. More specifically a heteroatom or carbon atom of the heterocycle may be modified to comprise the alkyl chain and functional groups. Exemplary modified bases are described in WO2009/037473 (the relevant contents of which are incorporated herein by reference).

In the context of the "modified bases", it is to be understood that the functional groups capable of "reversible covalent reactions" may be, for example, groups comprising aldehydes and/or ketones and in one embodiment, the reversible covalent reactions may involve reactions between the aldehyde/ketone groups of the modified base and amines, hydrazide and hydrazides (A. Dirksen, et al., *J. Am. Chem. Soc.,* 2006, 128, 15602-15603), alkoxyamine (V. A. Polyakov et al., *J. Phys. Org. Chem.* 1999, 12, 357-363) or alcohols, diols and/or boronic acids (O. Abed et al. *Chem. Mater.,* 2006, 18, 1247-1260). In one embodiment, the group capable of a reversible covalent reaction is not an alcohol.

The term "detectable tag" may be taken to encompass tags or labels which are, for example, distinguishable from one another either optically or otherwise. Many such tags or labels are known to those skilled in this field but, by way of example, suitable tags may include, for example, fluorescent or mass-tag compounds. More specifically, and in one embodiment, the modified bases/nucleobases of the present invention may comprise one or more detectable tag(s) (such as, for example a fluorophore) selected from a group of tags having optically detectable dyes ranging from, for example, the blue to the far-red spectra. Examples of tags which may be suitable include, for example, dansyl, fluorescein, rhodamine, texas red, IAEDANS, cyanine dyes (Cy3, Cy3.5, Cy5, Cy5.5, Cy7), Bodipy dyes (Invitrogen), SETA dyes such as SETA 425 (Seta Biomedicals) and/or Alexa Fluor dyes (Invitrogen).

Suitable "mass-tag" compounds may include, for example, tags which comprise bromide moieties or other compounds, molecules or moieties capable of providing a clear isotopic pattern in mass-spectrometry techniques such as, for example, MALDI-TOF. Where the modified base is a modified uracil base, the mass tag may not be bromine.

Accordingly, one of skill in the art will appreciate that any of the modified nucleobases described herein may be detected by, for example, fluorescent microscopy or mass spectrometry techniques such as MALDI-TOF or the like.

Advantageously, the heterocycle of each of the modified bases/nucleobases described herein may comprise a detectable tag linked, for example, at any number of positions through a heteroatom or a carbon atom. In one embodiment, the heteroatom may be modified so as to further comprise suitable spacer/carbon spacer moieties such as, for example an alkyne, alkenylene or alkynylene moiety which may be independently substituted with one or more of the detectable tags noted above. By way of example, the heteroatom and/or modified heteroatom of the heterocycle may comprise one or more fluorophore(s) (T. S. Seo et al., *PNAS,* 2004, 101, 5488-5493; Z. Li et al., *PNAS,* 2003, 100, 414-419; L. Thoresen et al., *Chem. Eur. J.* 2003, 9, 4603-4610) and/or mass tags i.e. bromide, chloride (C. Portal et al., *J. Comb. Chem.,* 2005, 7, 554-560). In one embodiment, the purine and/or pyrimidine heterocycles may be modified by, for example, cross coupling reactions using palladium catalysts (L. Thoresen et al., *Chem. Eur. J.* 2003, 9, 4603-4610; N. K. Garg et al. *Chem. Commun.,* 2005, 4551-4553).

Advantageously, each modified base/nucleobase may comprise a different detectable tag. In this way, the detectable tag may allow, for example, a modified adenine nucleobase to be distinguished from any other modified nucleobase.

A/the PNA monomer may have the general formula:

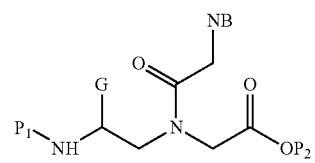

Formula (Ia)

wherein: G is a charged moiety, or a moiety capable of carrying a charge at a predetermined pH;
P$_1$ is a protective group P, or is hydrogen;
P$_2$ is a protective group P, or is hydrogen, or is a group selected from the list consisting of alkyl, cycloalkyl, aryl, aralkyl, or halogen; and
NB is a nucleobase.

A/the PNA monomer may have the general formula:

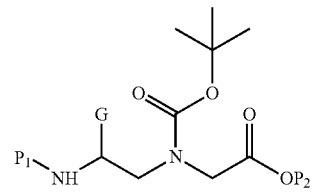

Formula (Ib)

wherein: G is a charged moiety, or a moiety capable of carrying a charge at a predetermined pH;
P$_1$ is a protective group P, or is hydrogen; and
P$_2$ is a protective group P, or is hydrogen, or is a group selected from the list consisting of alkyl, cycloalkyl, aryl, aralkyl, or halogen.

Thus, the PNA monomer of formula (Ib) may be described as a "blank" or "abasic" monomer, comprising a Boc protective group in place of a nucleobase.

Typically, either of the N-terminal and/or C-terminal positions may be derivatised so as to comprise a protecting group (as described above). Thus, the PNA monomer may be protected and/or may comprise a protective group P either at the N-terminal or C-terminal position.

If P$_1$ is a protective group P, then P$_2$ is hydrogen, and vice versa.

P$_1$ may be a protective group P, and P$_2$ may be hydrogen. In such instance, the PNA monomer may have the general formula:

Formula (Ic)

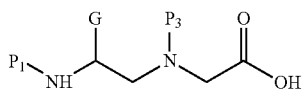

When G is a charged moiety, G may comprise one or more negative charges, and/or G may comprise one or more positive charges.

In one embodiment, G may comprise one negative charge or one positive charge.

G may comprise one or more one or more negatively charged groups selected from the group consisting of carboxylate, sulphonate, sulphate, phosphonate, phosphate.

G may comprise one or more one or more positively charged groups selected from the group consisting of guanidinium, quaternary ammonium, phosphonium, sulphonium.

G may comprise one or more groups, e.g. neutral groups which may not carry a charge at a first pH, but may be capable of carrying a charge at a second or predetermined pH. In such instance G may be selected from the group consisting of amine, hydrazide, hydrazine, guanidine, alkoxyamine, sulphonic acids and/or derivatives thereof, and/or phosphonic acids and/or derivatives thereof.

G may comprise one or more groups capable of carrying a first charge, e.g., a negative charge, at a first pH or pH range, and a second charge, e.g., a positive charge, at a second pH or pH range.

It will be understood that the skilled person may select a suitable group "G" based on the conditions intended during use of the PNA oligomer from which the PNA monomer is derived. In particular, when the resulting PNA oligomer is intended for use in an assay, a suitable group "G" may be selected by the skilled person such that group "G" will carry a charge moiety at the pH environment of the assay.

When G is a group capable of carrying a charge at a predetermined pH, the pH at which the group G is capable of carrying a charge may be in the range of 6-8

When G is capable of carrying a negative charge, the pH at which the group G is capable of carrying the negative charge may be in the range of 6-8.

When G is capable of carrying a positive charge, the pH at which the group G is capable of carrying the positive charge may be in the range of 6-8.

In some embodiments, the group G capable of carrying a negative charge at a predetermined pH may comprise an acid and/or derivative thereof, e.g., an ester. The group G may comprise a carboxylic acid or derivative thereof, a sulphonic acid or derivative thereof, a sulphuric acid or derivative thereof, a phosphonic acid or derivative thereof, a phosphoric acid or derivative thereof.

In some embodiments, the group G capable of carrying a positive charge at a predetermined pH may comprise a base and/or derivative thereof. The group G may comprise an amine, a hydrazide, a hydrazine, a guanidinium, an alkoxyamine, and/or derivative thereof.

In one embodiment, G may have the general formula:

Formula (III)

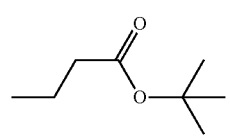

In such instance, the PNA monomer may have the general formula:

Formula (Id)

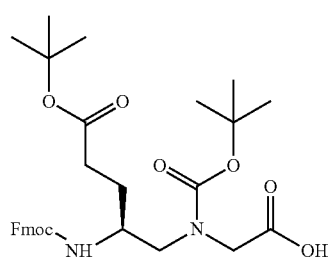

wherein: Fmoc is fluorenylmethoxycarbonyl.

According to a second aspect of the invention, there is provided a PNA monomer having the general formula:

Formula (I)

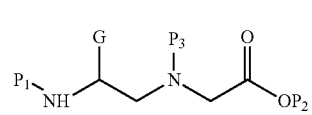

wherein: G is a charged moiety, or a moiety capable of carrying a charge at a predetermined pH;

$P_1$ is a protective group P, or is hydrogen;

$P_2$ is a protective group P, or is hydrogen, or is a group selected from the list consisting of alkyl, cycloalkyl, aryl, aralkyl, or halogen, $P_3$ is hydrogen, or is a protective group P, or is a group represented by formula (II) below:

Formula (II)

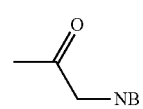

wherein NB is a nucleobase.

In one embodiment, $P_3$ is not a group represented by formula (II). In such instance $P_3$ may be a protective group P or may be hydrogen.

The features described in respect of any other aspect of the invention may equally apply in respect of the PNA monomer according to the second aspect of the invention, and are not repeated here for reasons of brevity.

According to a third aspect of the invention, there is provided a PNA dimer comprising, at at least one gamma position, a charged moiety or a moiety capable of carrying a charge at a predetermined pH.

The PNA dimer may be derived from a glycine unit.

Typically, the PNA dimer may be derived from a N-(2-aminoethyl)-glycine unit. As stated, the PNA dimer may comprise at the gamma position of one or both repeat units a charged moiety, or a moiety capable of carrying a charge at a predetermined pH.

The PNA dimer may have the general formula:

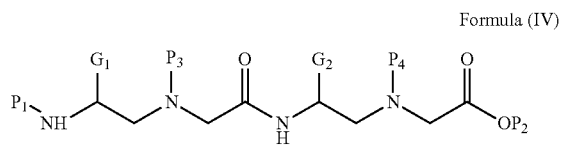

Formula (IV)

wherein: $G_1$ and $G_2$ are independently hydrogen or G, wherein G is a charged moiety, or a moiety capable of carrying a charge at a predetermined pH;
$P_1$ is a protective group P, or is hydrogen;
$P_2$ is a protective group P, or is hydrogen, or is a group selected from the list consisting of alkyl, cycloalkyl, aryl, aralkyl, or halogen,
$P_3$ is hydrogen, or is a protective group P, or is a group represented by formula (II) below;

Formula (II)

wherein NB is a nucleobase;
with the proviso that
at least one of $G_1$ and $G_2$ is G,
if $P_3$ is hydrogen or a protective group P, then $G_1$=G, and
if $P_4$ is hydrogen or a protective group P, then $G_2$=G.

When G is a charged moiety, G may comprise one or more negative charges, and/or G may comprise one or more positive charges.

In one embodiment, G may comprise one negative charge or one positive charge.

G may comprise one or more one or more negatively charged groups selected from the group consisting of carboxylate, sulphonate, sulphate, phosphonate, phosphate. G may comprise one or more one or more positively charged groups selected from the group consisting of guanidinium, quaternary ammonium, phosphonium, or sulphonium.

G may comprise one or more groups, e.g. neutral groups which may not carry a charge at a first pH, but may be capable of carrying a charge at a second or predetermined pH. In such instance G may be selected from the group consisting of amine, hydrazide, hydrazine, guanidine, alkoxyamine, sulphonic acids and/or derivatives thereof, and/or phosphonic acids and/or derivatives thereof.

G may comprise one or more groups capable of carrying a first charge, e.g., a negative charge, at a first pH or pH range, and/or a second charge, e.g., a positive charge, at a second pH or pH range.

It will be understood that the skilled person may select a suitable group "G" based on the conditions intended during use of the PNA oligomer from which the PNA monomer is derived. In particular, when the resulting PNA oligomer is intended for use in an assay, a suitable group "G" may be selected by the skilled person such that group "G" will carry a charge moiety at the pH environment of the assay.

When G is a group capable of carrying a charge at a predetermined pH, the pH at which the group G is capable of carrying a charge may be in the range of 6-8.

When G is capable of carrying a negative charge, the pH at which the group G is capable of carrying the negative charge may be in the range of 6-8.

When G is capable of carrying a positive charge, the pH at which the group G is capable of carrying the positive charge may be in the range of 6-8.

In some embodiments, the group G capable of carrying a negative charge at a predetermined pH may comprise an acid and/or derivative thereof, e.g., an ester. The group G may comprise a carboxylic acid or derivative thereof, a sulphonic acid or derivative thereof, a sulphuric acid or derivative thereof, a phosphonic acid or derivative thereof, a phosphoric acid or derivative thereof. In some embodiments, the group G capable of carrying a positive charge at a predetermined pH may comprise a base and/or derivative thereof. The group G may comprise an amine, a hydrazide, a hydrazine, a guanidinium, an alkoxyamine, and/or derivative thereof.

In one embodiment, G may have the general formula:

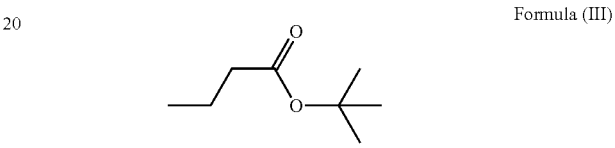

Formula (III)

Typically, either of the N-terminal and/or C-terminal positions may be derivatised so as to comprise a protecting group (as described above). Thus, the PNA monomer may be protected and/or may comprise a protective group P either at the N- or C-terminal position.

In one embodiment, if $P_1$ is a protective group P, then $P_2$ is hydrogen, and vice versa.

In a preferred embodiment, $P_1$ is a protective group P, and $P_2$ is hydrogen.

The features described in respect of any other aspect of the invention may equally apply in respect of the PNA dimer according to the third aspect of the invention, and are not repeated here for reasons of brevity.

According to a fourth aspect of the invention, there is provided a PNA dimer having the general formula:

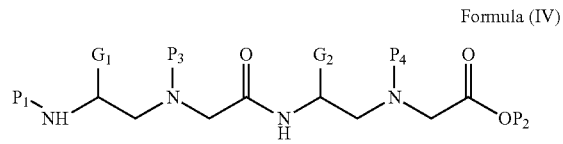

Formula (IV)

wherein: $G_1$ and $G_2$ are independently hydrogen or G, wherein G is a charged moiety, or a moiety capable of carrying a charge at a predetermined pH;
$P_1$ is a protective group P, or is hydrogen;
$P_2$ is a protective group P, or is hydrogen, or is a group selected from the list consisting of alkyl, cycloalkyl, aryl, aralkyl, or halogen,
$P_3$ is hydrogen, or is a protective group P, or is a group represented by formula (II) below;

Formula (II)

wherein NB is a nucleobase;
with the proviso that
at least one of $G_1$ and $G_2$ is G,
if $P_3$ is hydrogen or a protective group P, then $G_1$=G, and
if $P_4$ is hydrogen or a protective group P, then $G_2$=G.

The features described in respect of any other aspect of the invention may equally apply in respect of the PNA dimer according to the fourth aspect of the invention, and are not repeated here for reasons of brevity.

According to a fifth aspect of the invention, there is provided a PNA oligomer, wherein at least one repeat unit comprises at its gamma position a charged moiety or a moiety capable of carrying a charge at a predetermined pH.

Typically, the PNA monomer from which the PNA oligomer is derived, or one or more repeat units of the PNA oligomer, is/are derived from a N-(2-aminoethyl)-glycine unit. As stated, the PNA monomer or one or more of the repeat units of the PNA oligomer may comprise at the/their gamma position(s) a charged moiety, or a moiety capable of carrying a charge at a predetermined pH.

The PNA oligomer may have the general formula:

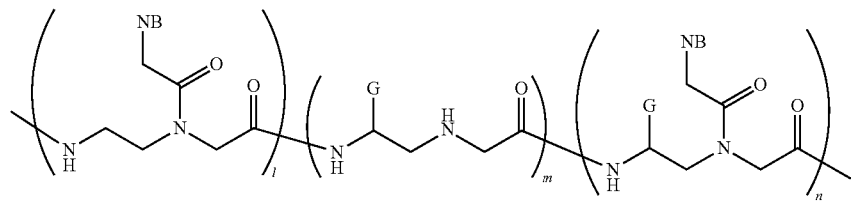

Formula (V)

wherein: G is a charged moiety, or a moiety capable of carrying a charge at a predetermined pH;
NB is a nucleobase; and
$l≥0$; $m≥0$; $n≥0$, with the proviso that $l+m+n≥2$ and $n+m≥1$.
Preferably, $l≥1$.
Preferably, $m≥1$.
Typically, $m=1$.
Preferably, $n≥1$.

It will be understood that the repeat units of the PNA oligomer of formula (V) may not necessarily be provided sequentially or as a block polymer of blocks l, m, and n, but that the repeat units may be provided in any order.

Typically, the total number of PNA units (l+m+n) in the oligomer may be in the range of 5-50, e.g. 7-40, e.g. 10-30, typically 12-24.

It will be appreciated that the number of repeat units comprising at their respective gamma positions a charged moiety or a moiety capable of carrying a charge at a predetermined pH, and/or the number of units having a "G" moiety in formula (V), may depend on the particular application envisaged for the PNA molecule, e.g., PNA oligomer.

Typically, the number of repeat units comprising at their respective gamma positions a charged moiety or a moiety capable of carrying a charge at a predetermined pH, and/or the number of units having a "G" moiety in formula (V), may be in the range of 1-10, e.g., 2-8, e.g., 3-5. Stated differently, (n+m) may be in the range of 1-10, e.g., 2-8, e.g., 3-5.

For example, it was observed that, for PNA molecules/oligomers having approximately 12-22 repeat units, a number of repeat units comprising at their respective gamma positions a charged moiety or a moiety capable of carrying a charge at a predetermined pH, and/or the number of units having a "G" moiety in formula (V), in the range of 3-5, provided significantly improved performance.

The ratio of the number of repeat units comprising at their respective gamma positions a charged moiety or a moiety capable of carrying a charge at a predetermined pH and/or of the number of units having a "G" moiety in formula (V), to the total number of repeat units, may be in the range of 1:20-1:1, typically, 1:10-1:2. e.g., 1:5-1:2.

The ratio (n+m)/(l+m+n) may be in the range of 1:20-1:1, typically, 1:10-1:2. e.g., 1:5-1:2.

Typically, when the PNA molecule comprises a "blank" or "abasic" unit, the "blank" or "abasic" unit comprises at the gamma position a charged moiety or a moiety capable of carrying a charge at a predetermined pH. It was observed that the provision of a charged moiety or a moiety capable of carrying a charge at a predetermined pH, at the gamma position of the "blank" or "abasic" unit, provided significantly improved performance of the PNA molecule.

Typically, m=1.

The repeat units comprising the gamma position a charged moiety or a moiety capable of carrying a charge at a predetermined pH, may be distributed in the PNA molecule so as to provide optimum stability and/or performance.

The PNA oligomer may comprise at least a portion in which each repeat unit comprising at its gamma position a charged moiety or a moiety capable of carrying a charge at a predetermined pH is distributed in the portion of the PNA oligomer every 1-5, e.g., every 2-4 units.

Where the PNA molecule comprises a "blank" or "abasic" unit comprising at the gamma position a charged moiety or a moiety capable of carrying a charge at a predetermined pH, the PNA oligomer comprises at least a portion adjacent or around the "blank" or "abasic" unit, in which each repeat unit comprising at its gamma position a charged moiety or a moiety capable of carrying a charge at a predetermined pH, is distributed in that portion every 1-5, e.g., every 2-4 units.

Without wishing to be bound by theory, it is suggested that the presence and/or distribution of "modified" units near or around the "blank" or "abasic" unit, may improve the dimensional stability and/or performance of the PNA molecule, e.g., PNA oligomer.

The "blank" or "abasic" unit may be located distal from one or more ends of the PNA oligomer. Typically, the "blank" or "abasic" unit may be located at least one, e.g., at least two, e.g. at least three repeat units from one or more ends, preferably from both ends, of the PNA oligomer. By such provision, the performance of the probe may be improved. It will be appreciated that the exact location of the "blank" or "abasic" unit within the PNA oligomer, and/or the distance of the "blank" or "abasic" unit relative to one or more ends of the PNA oligomer, may depend on the overall length of the PNA oligomer and the specific application intended for the probe.

When G is a charged moiety, G may comprise one or more negative charges, and/or G may comprise one or more positive charges.

In one embodiment, G may comprise one negative charge or one positive charge.

G may comprise one or more one or more negatively charged groups selected from the group consisting of carboxylate, sulphonate, sulphate, phosphonate, phosphate.

G may comprise one or more one or more positively charged groups selected from the group consisting of guanidinium, quaternary ammonium, phosphonium, or sulphonium, G may comprise one or more groups, e.g. neutral groups which may not carry a charge at a first pH, but may be capable of carrying a charge at a second or predetermined pH. In such instance G may be selected from the group consisting of amine, hydrazide, hydrazine, guanidine, alkoxyamine, sulphonic acids and/or derivatives thereof, and/or phosphonic acids and/or derivatives thereof.

G may comprise one or more groups capable of carrying a first charge, e.g., a negative charge, at a first pH or pH range, and/or a second charge, e.g., a positive charge, at a second pH or pH range.

It will be understood that the skilled person may select a suitable group "G" based on the conditions intended during use of the PNA oligomer from which the PNA monomer is derived. In particular, when the resulting PNA oligomer is intended for use in an assay, a suitable group "G" may be selected by the skilled person such that group "G" will carry a charge moiety at the pH environment of the assay.

When G is a group capable of carrying a charge at a predetermined pH, the pH at which the group G is capable of carrying a charge may be in the range of 6-8.

When G is capable of carrying a negative charge, the pH at which the group G is capable of carrying the negative charge may be in the range of 6-8.

When G is capable of carrying a positive charge, the pH at which the group G is capable of carrying the positive charge may be in the range of 6-8.

In some embodiments, the group G capable of carrying a negative charge at a predetermined pH may comprise an acid and/or derivative thereof, e.g., an ester. The group G may comprise a carboxylic acid or derivative thereof, a sulphonic acid or derivative thereof, a sulphuric acid or derivative thereof, a phosphonic acid or derivative thereof, a phosphoric acid or derivative thereof.

In some embodiments, the group G capable of carrying a positive charge at a predetermined pH may comprise a base and/or derivative thereof. The group G may comprise an amine, a hydrazide, a hydrazine, a guanidinium, an alkoxyamine, and/or derivative thereof.

In one embodiment, G may have the general formula:

Formula (III)

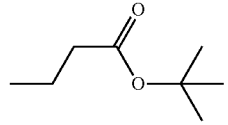

A PNA molecule, for example a PNA oligomer, described herein may be attached to, bound to and/or associated with a support.

In one embodiment, the PNA molecule may be covalently attached to the support.

The support may comprise a solid support.

The support may be provided in the form of a 2-dimensional and/or substantially planar surface, such as a membrane, a film, a sheet, or the like.

The support may comprise a membrane. The membrane may comprise a polymer-based membrane, such as nylon or a nylon-functionalised membrane.

The support may comprise a silicate surface. The silicate surface may comprise a functionalised glass surface or a silicon surface. The support may be provided in the form of a particle, bead, or the like. In such instance the support may comprise a resin support, such as a cross-linked polystyrene microbeads, cross-linked polystyrene paramagnetic microbeads, cross-linked polystyrene coloured tagged microbeads (e.g., from Luminex Inc.), polystyrene latex beads, or the like. The support, e.g. 2-dimensional support and/or particulate support, may comprise and/or may be made of a surface-modified material, e.g., a surface-modified resin. The material may comprise a surface modified to incorporate chemical groups capable of binding, e.g., covalently binding to the PNA molecule at either the N-terminal or C-terminal positions or a component thereof (for example a PNA monomer from which the PNA oligomer is derived).

The features described in respect of any other aspect of the invention may equally apply in respect of the PNA oligomer according to the fifth aspect of the invention, and are not repeated here for reasons of brevity.

According to a sixth aspect of the invention, there is provided a PNA oligomer having the general formula:

Formula (V)

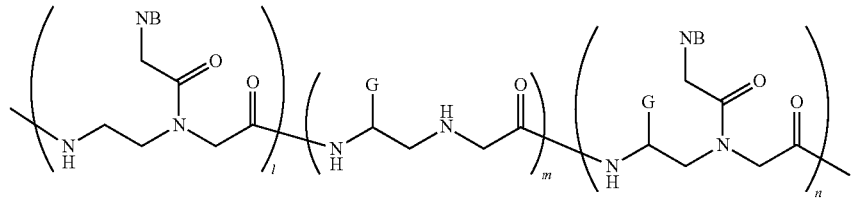

wherein: G is a charged moiety, or a moiety capable of carrying a charge at a predetermined pH;
NB is a nucleobase; and
$l≥0$; $m≥0$; $n≥0$, with the proviso that $l+m+n≥2$ and $n+m≥1$.
Preferably, $l≥1$.
Preferably, $m≥1$.
Typically, $m=1$.
Preferably, $n≥1$.
It will be understood that the repeat units of the PNA oligomer of formula (V) may not necessarily be provided sequentially or as a block polymer of blocks l, m, and n, but that the repeat units may be provided in any order.

Typically, the total number of PNA units (l+m+n) in the oligomer may be in the range of 5-50, e.g. 7-40, e.g. 10-30, typically 12-24.

The features described in respect of any other aspect of the invention may equally apply in respect of the PNA oligomer according to the sixth aspect of the invention, and are not repeated here for reasons of brevity.

According to a seventh aspect of the present invention, there is provided a use for a modified PNA molecule (for example PNA oligomer) as described herein, in a genetic or nucleic acid analysis method.

It is to be understood that the terms "genetic" or "nucleic" analysis methods may embrace, for example, methods aimed at the characterisation, identification and/or sequencing of nucleobases of nucleic acids. In one embodiment, such methods may be used to characterise individual nucleotides, single nucleotide polymorphisms (SNP) and/or to sequencing nucleic acids.

Accordingly, the phrase "characterising a nucleobase" may be taken to encompass the act of identifying or determining a particular nucleobase of a particular nucleic acid sequence—in other words, identifying which nucleobase a particular nucleotide comprises. In instances where the methods are used to characterise a SNP, the term "characterise" may be taken to encompass the act of determining which particular SNP allele (or nucleobase) is present in a particular nucleic acid sequence.

In a preferred embodiment, a modified PNA molecule (for example a PNA oligomer) for use in a genetic analysis method (for example a method of characterising one or more nucleotides(s) in a nucleic acid sequence) may lack a base complementary to that of the nucleotide to be characterised. In such instance, the PNA oligomer may be described as comprising a "blank" or "abasic" PNA unit.

The features described in respect of any other aspect of the invention may equally apply in respect of the use according to the seventh aspect of the invention, and are not repeated here for reasons of brevity.

According to an eighth aspect of the invention, there is provided a method for preparing a PNA molecule, for example a PNA monomer according to a first or second aspect of the invention, the method comprising:

providing a compound according to formula (A3);

reacting the compound of formula (A3) either with a nucleobase-containing acid derivative, or with a protective group P; and hydrolysing.

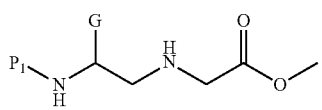

A3 wherein G is a charged moiety, or a moiety capable of carrying a charge at a predetermined pH, and wherein $P_1$ is a protective group.

The nucleobase-containing acid derivative may be a compound according to formula NB-1.

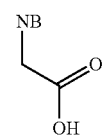

NB-1 wherein NB is a nucleobase.

Thus, the method may comprise a reaction according to scheme 1:

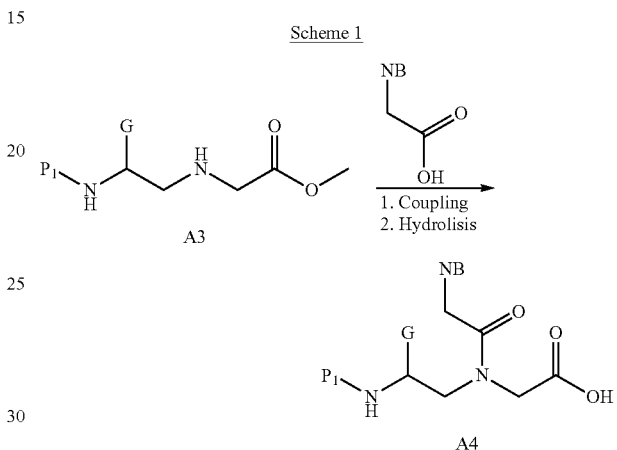

In one embodiment, the protective group P introduced in the compound of formula (A3) may be a Boc protective group.

In one embodiment, the protective group $P_1$ may be Fmoc.

The method may comprise a reaction according to scheme 2:

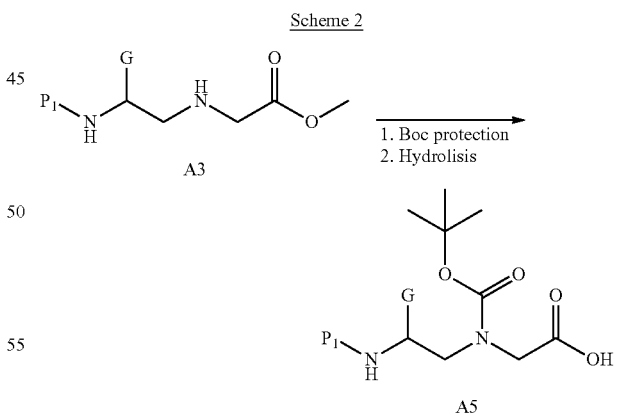

Thus, the compound of formula (A5) may be termed an abasic or "blank" PNA monomer.

The method may comprise preparing the compound of formula (A3).

The method may comprise amination of an N-protected alpha-modified glycinal compound, such as a compound according to formula (A1).

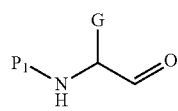

A1

The amination may comprise reacting the N-protected alpha-modified glycinal compound, e.g., the compound according to formula (A1), with glycine methyl ester.

The amination reaction according to scheme 3:

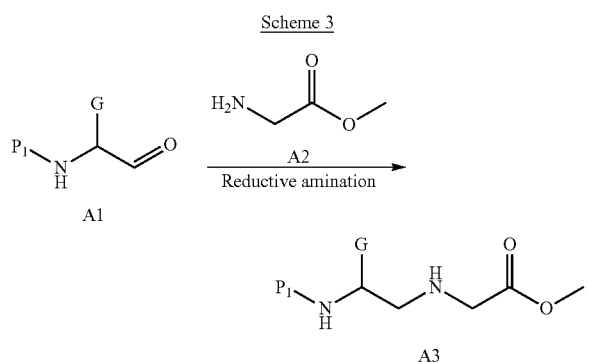

The method may comprise preparing the compound of formula (A1).

The method may comprise oxidation of a compound according to formula (A0).

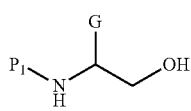

A0

The oxidation may comprise a reaction according to scheme 4.

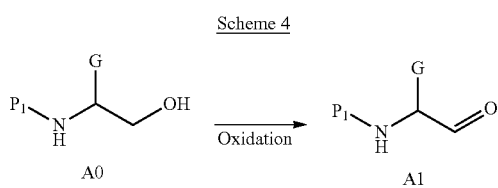

Typically, either of the N-terminal and/or C-terminal positions may be derivatised so as to comprise a protecting group (as described above). Thus, the PNA monomer may be protected and/or may comprise a protective group P either at the N- or C-terminal position.

In one embodiment, if $P_1$ is a protective group P, then $P_2$ is hydrogen, and vice versa.

In a preferred embodiment, $P_1$ is a protective group P, and $P_2$ is hydrogen. In such instance, the PNA monomer may have the general formula:

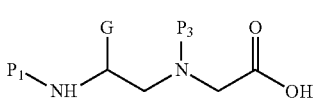

Formula (Ic)

The features described in respect of any other aspect of the invention may equally apply in respect of the method according to the eighth aspect of the invention, and are not repeated here for reasons of brevity.

According to a ninth aspect of the invention, there is provided a method for preparing a PNA oligomer according to a fifth or sixth of the invention, the method comprising reacting one or more PNA monomers according to a first or second aspect of the invention so as to form the PNA oligomer.

The method may comprise reacting one or more PNA monomers according to a first or second aspect of the invention (namely PNA monomers having a group "G" at the gamma position) with different PNA monomers, such as one or more PNA monomers not comprising a group "G" at the gamma position.

The method may comprise synthesising the PNA oligomer using one or more PNA monomers comprising a protective group P at the N-terminal. In one embodiment, the method may comprise synthesising the PNA oligomer using Dde-protected PNA monomers as taught in the method disclosed in Bradley et al., *Tetrahedron*, 2005, 61, 8295-8305, on solid phase (J. J. Diaz-Mochon et al., *Org. Lett.* 2004, 6, 1127-1129).

The method may comprise the preliminary step of immobilising a PNA monomer on a support, e.g. a solid support, for example through its C-terminal.

The method may comprise immobilising a PNA monomer through covalent bonding between a modified support and the C-end of the PNA monomer.

It will be appreciated that the PNA monomer immobilised on or bonded to the support may be a PNA monomer according to the first aspect of the invention, or a different PNA monomer not comprising a group "G" at the gamma position, depending on the position or positions in the PNA oligomer at which a charged moiety is intended to be located.

The features described in respect of any other aspect of the invention may equally apply in respect of the method according to the ninth aspect of the invention, and are not repeated here for reasons of brevity.

According to a tenth aspect of the invention, there is provided a method of characterising a nucleotide in a nucleic acid sequence, said method comprising the steps of:

(a) contacting a nucleic acid with a peptide nucleic acid (PNA) oligomer described herein, the PNA oligomer being capable of hybridising to a portion of the nucleic acid, to form a nucleic acid/PNA duplex; and (b) contacting the nucleic acid/PNA duplex with one or more modified bases selected from the group consisting of

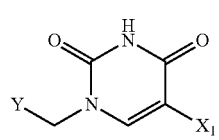

(i)

-continued (ii)

(iii)

(iv)

wherein Y is a functional group capable of reversible covalent reactions;

$X_1$-$X_4$ is a detectable tag, spacer-tag combination or hydrogen; and

Z is carbon or nitrogen;

wherein the PNA oligomer comprises a moiety capable of reacting reversibly with functional group Y and wherein the modified base which integrates with the nucleic acid/PNA duplex is complementary to that of the nucleotide to be characterised, the nucleotide being characterised by mass spectrometry or by means of the detectable tag of the modified base.

In a preferred embodiment, the PNA oligomer may be lacking a base complementary to that of the nucleotide to be characterised. In such instance, the PNA oligomer may be described as comprising a "blank" or "abasic" PNA unit.

The PNA oligomer may have the general formula:

Formula (VII)

wherein: G is a charged moiety, or a moiety capable of carrying a charge at a predetermined pH;

NB is a nucleobase; and $l \geq 1$; $m \geq 0$; $n \geq 0$, with the proviso that $l+m+n \geq 2$ and $n+m \geq 1$.

Preferably, $m \geq 1$.

Typically, $m=1$.

Preferably, $n \geq 1$.

In one embodiment, the PNA molecule may be attached to a support. Typically, the PNA molecule may be covalently attached to the support.

The support may comprise a solid support, for example, a support as described in respect of the PNA oligomer according to a fifth aspect of the invention.

The features described in respect of any other aspect of the invention may equally apply in respect of the method according to the tenth aspect of the invention, and are not repeated here for reasons of brevity.

BRIEF DESCRIPTION OF DRAWINGS

The present invention will now be described in detail and with reference to the following Figures which show:

FIG. 6: Results of the intensity measured for the PNA molecules of FIG. 5;

FIG. 9: Results of the intensity measured for alternative embodiments of the PNA molecules;

FIG. 14: Flow cytometry analyses of the PNA oligomers described in Table 2 (see below). A) Microsphere labelling was conducted using microspheres containing the PNA oligomer DGL 21_6.0, SMART-A-Nucleobase-Biotin and Oligo DNA 21 (15 nM); B) As negative control water (no labelling).

FIG. 15: Flow cytometry analyses of PNA oligomers reported in Table 2 (see below). Microsphere labelling was conducted using microspheres containing the PNA oligomer DGL 21_2.0 (A) and DGL 21_3.0 (B), SMART-A-Nucleobase-Biotin and oligo DNA 21 (15 nM).

FIG. 16: PNA molecules for circulating microRNA 122. Six PNA Oligomers with sequence of nucleobases complementary to the mature miRNA122 strand. Oligomers contained unmodified PNA monomers (open circles) and monomers containing chiral modifications at gamma-positions a moiety containing a carboxylic acid group (filled circles). Either filled and empty ellipses show the abasic unit respectively with or without modifications at gamma positions.

FIG. 17: Three PNA molecules for circulating microRNA 21. See FIG. 16 for the legend.

EXAMPLES

Preparation
Monomer Preparation

Gamma-modified nucleobase-containing and "blank" PNA monomers of the present invention were prepared.

In this embodiment, the PNA monomers were based on a (L) Glutamic amino derivative.

In this embodiment, a nucleobase-containing gamma-modified PNA monomer (A8) and a "blank" gamma-modified PNA monomer (A9) were prepared as follows.

In a first step, a gamma-modified compound of formula (A7) was prepared by 1) oxidation and 2) reductive amination of (L) Fmoc-Glutamol of formula (A6). The alcohol was oxidised to aldehyde (IBX or DMP), which was then reacted with glycine methyl ester (A2) under reductive amination conditions to yield the gamma-modified compound (A7).

In a second step, the gamma-modified compound (A7) was reacted to yield either a nucleobase-containing PNA monomer (A8) or a "blank" PNA monomer (A9).

To prepare a nucleobase-containing PNA monomer (A8), the gamma glutamic compound (A7) was coupled a nucleobase (A, C, G, T) and then treated under hydrolysis conditions to yield the gamma-modified nucleobase-containing PNA monomer (A8).

To prepare the chiral "blank" PNA monomer (A9), the secondary amine of the compound (A7) was protected with a protective group, in this embodiment Boc, and the resulting product treated under hydrolysis conditions to obtain the "blankPNA" monomer (A9).

Figure 1:
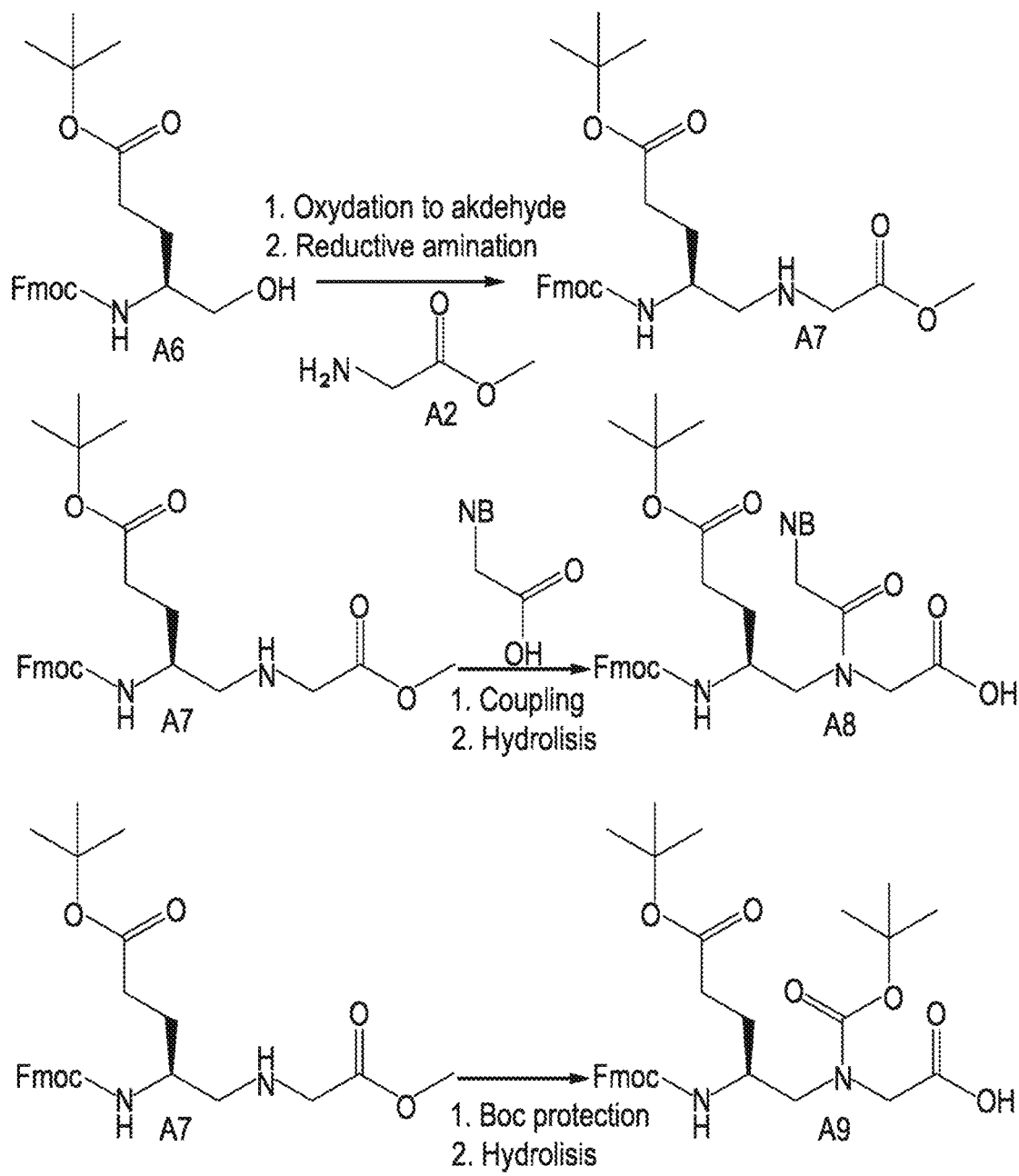
FIG. 1: Reactions schemes used to prepare a PNA monomer according to an embodiment of the invention.

This is illustrated in the reaction schemes of FIG. 1.
PNA Molecules

Various PNA molecules, including PNA oligomers containing and/or derived from monomers A8 and A9 above, were prepared and assessed.

Figure 2:
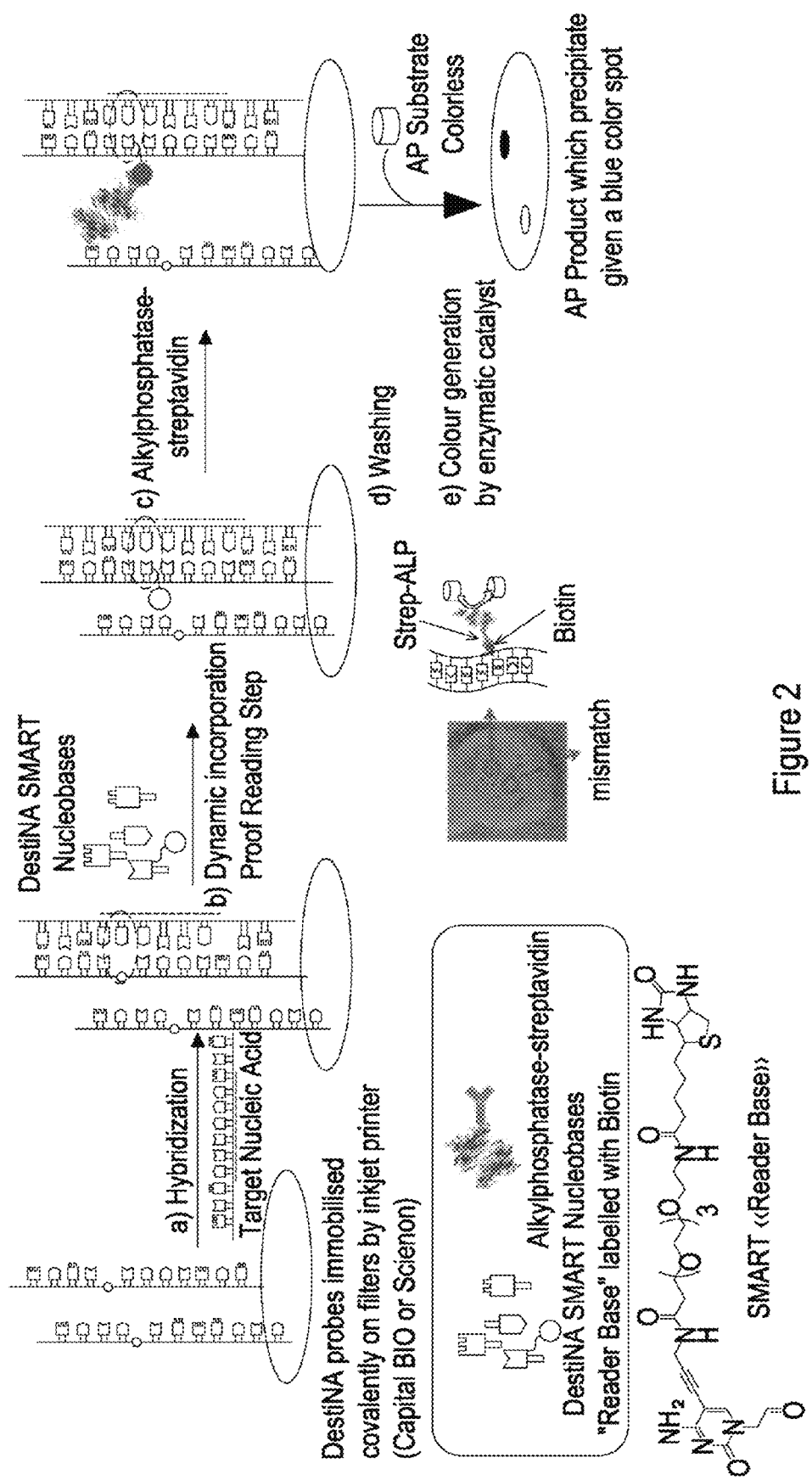
FIG. 2: Scheme representing a colorimetric approach to test PNA probes.

In order to assess the specificity and sensitivity of the PNA molecules, a SMART C Nucleobase modified with a biotin was used. A colorimetric approach (as shown in the scheme of FIG. 2) was performed using PNA probes supported on nylon membranes through an amino-pegylated group at their N-terminal end.

Figure 3:
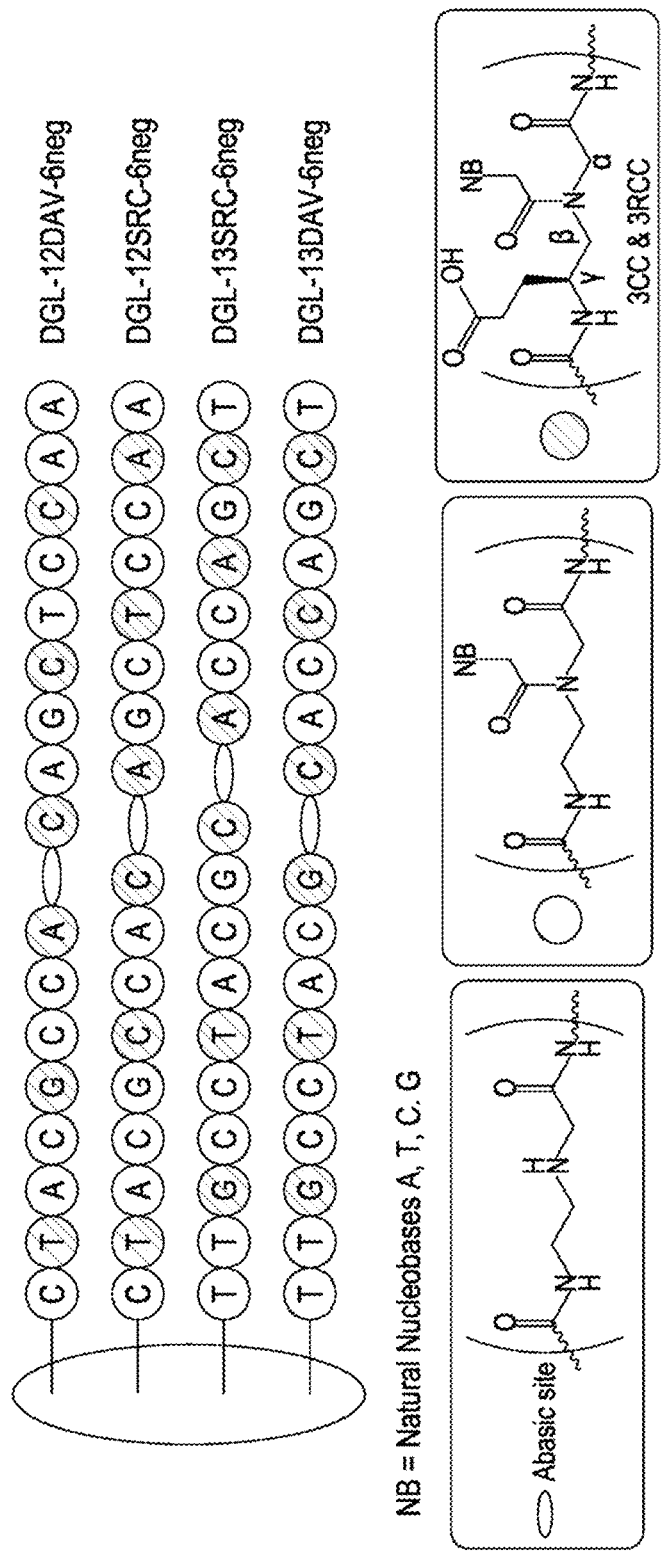
FIG. 3: Examples of PNA molecules tested.

In this method, DestiNA probes (from 10 to 100 µM solutions) modified at their N-terminal with an amino-pegylated group were immobilised onto Immunodyne ABC (activated nylon 6.6 membranes from Pall). DestiNA master mix was prepared with 30 µL of SMART-C-PEG-Biotin (SMART "Reader Base") (100 µM), 45 µL of nucleic acid strands (KWT DNA and K12S DNA) at 100 nM or 45 uL PCR KWT and K12S and 20 µL of reducing agent, sodium cyanoborohydride (15 mM) and 205 µL of citrate buffer 0.1M with 0.1% SDS (pH 6). DestiNA master mix was then added onto the spotted membrane and incubated at 41° C. for 20 to 30 min. The membranes were then washed twice with 0.5× saline sodium citrate (SSC) and 0.5% sodium dodecyl sulfate (SDS) using a vacuum manifold. The membrane was blocked with a blocking solution with BSA and casein for 5 min and then, streptavidin-alkaline phosphatase solution was added onto the membrane and incubated at 29° C. for 5 min. The membranes were then washed four times with tris-HCl 0.1M/tween 20 0.5% using a vacuum manifold. Finally, NBT/BCIP chromogenic solution was added and incubated at 36° C. for 8 min. Following washing steps, photographs of the membranes were taken and the intensity of the response measured. Images were taken by a LifeCam assisted with LED illumination. Signal intensities were measured by a densitometry image software. Signal values are arbitrary units related to biotin marker intensities within the same membrane.

a) PNA Molecules Containing 6 Gamma-Modified Units, and "Unmodified" Abasic Position Four different PNA probes (shown in FIG. 3) containing 6 gamma-modified units (represented in black) with an "unmodified" abasic position were immobilised on nylon membranes and tested.

In particular, the repeat units shown in white were devoid of any substituent at the gamma position, and the repeat units shown in black had at their gamma position a moiety containing a carboxylic acid group.

Specificity and Sensitivity of the probes were assessed as follows:

(I) SPECIFICITY: the highest signal differences between two PNA probes, when reacted with:
(a) KWT DNA (positive control—portion of the nucleic acid strand which contains as the nucleotide to be characterised a "G"; this nucleotide is thus characterised by means of the detectable tag carried by the modified nucleobase, in this case, following Watson and Crick pair ruling, the modified base is "C") or
(b) K12S DNA (negative control—portion of the nucleic acid strand which contains as the nucleotide to be characterised a "A"; this nucleotide should thus not be characterised by means of the detectable tag carried by the modified nucleobase as its complementary modified base "T" does not carry a detectable tag).

(ii) SENSITIVITY: signals given by the four probes tested 12SRC-12DAV-13SRC-13DAV should be similar when using DNA KWT.

Figure 4:
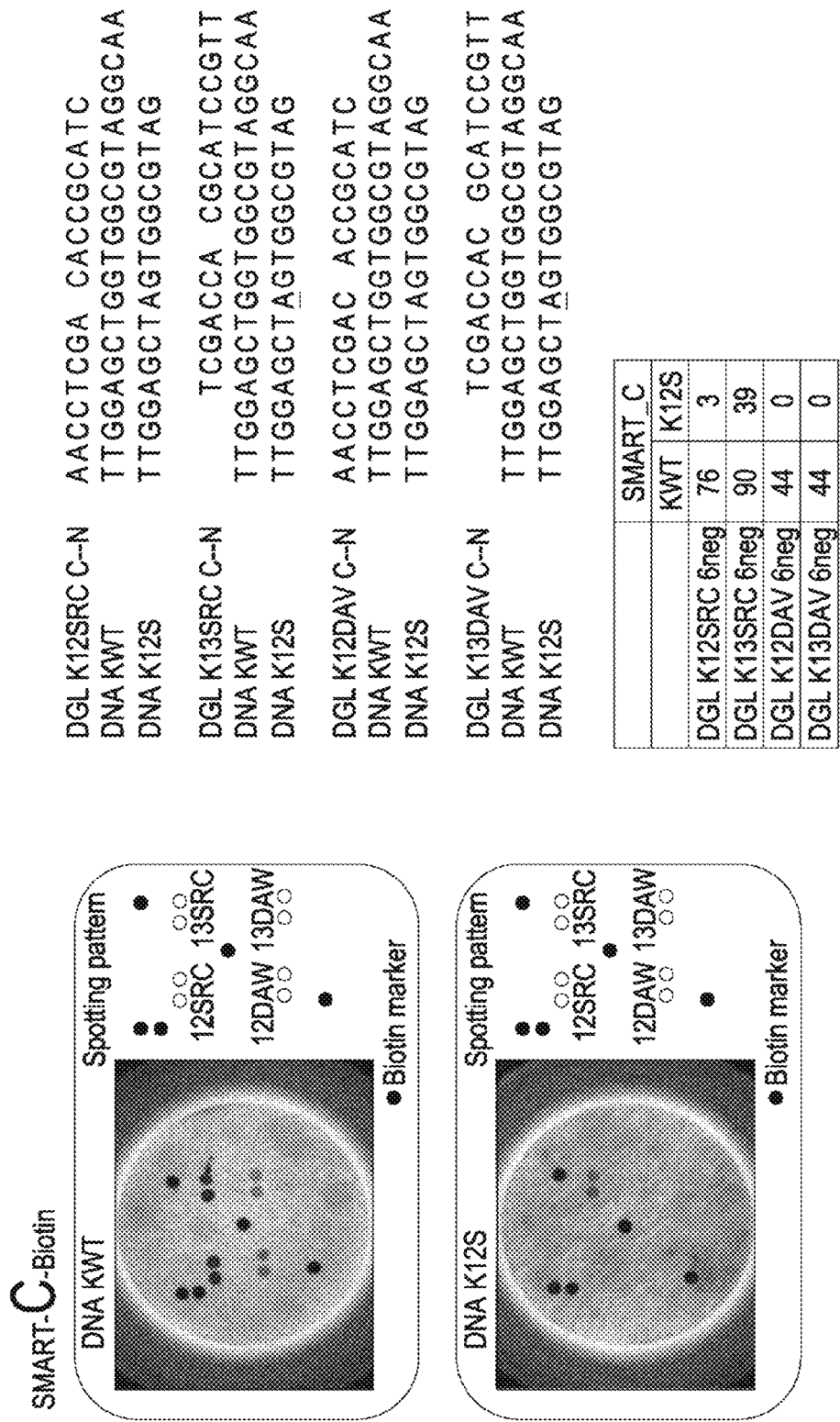
FIG. 4: Results of the intensity measured for the PNA molecules of FIG. 3.

The specific structure of the KWT DNA positive control and of the K12S negative control DNA; and the results of the signals measured for each probe, are shown in FIG. 4.

In FIG. 4, DNA from PCR amplification and PNA (DGL) sequences are aligned. Mismatch nucleotides are underlined. Probes were spotted at 100 µM.

Figure 5:
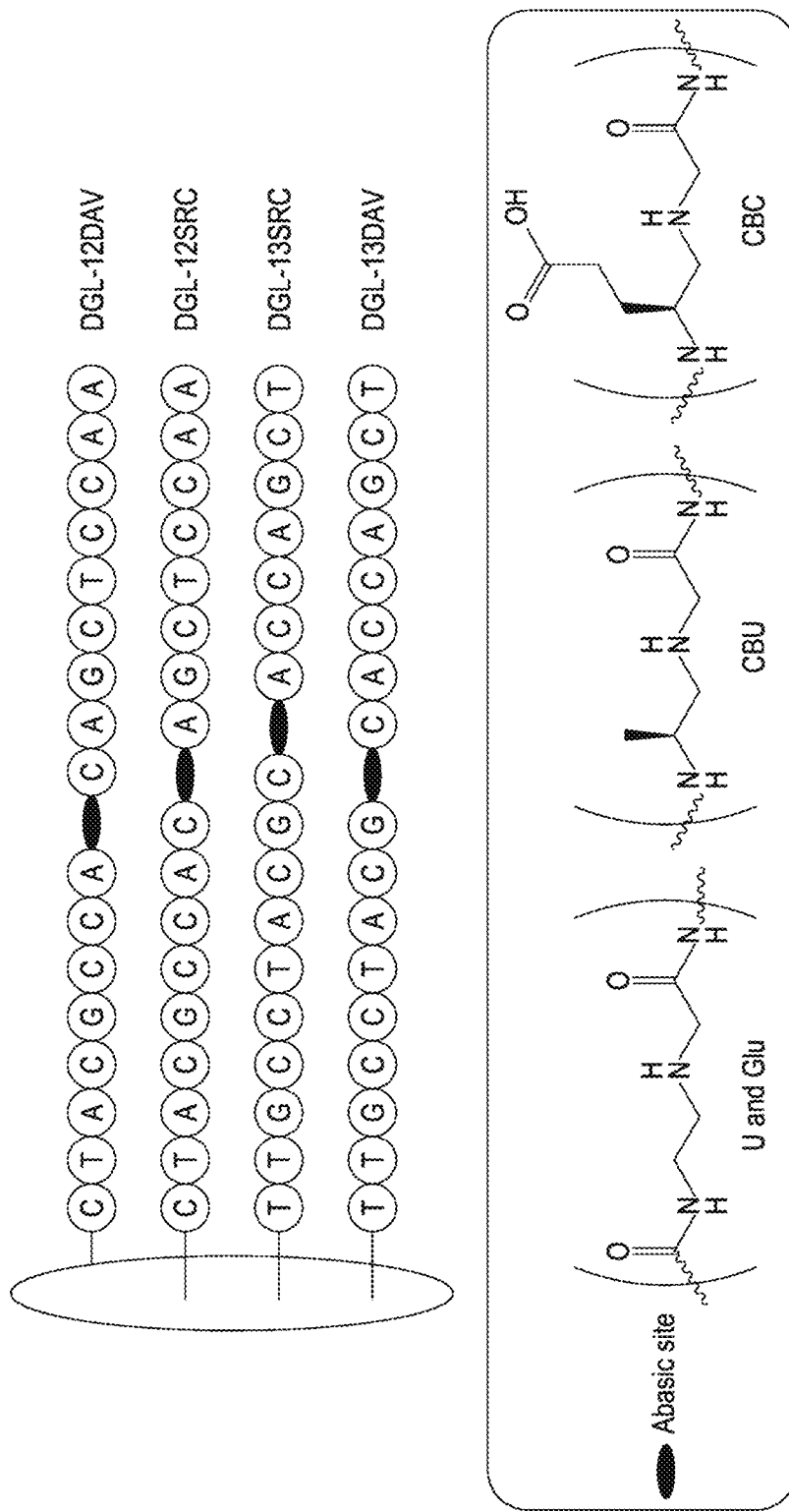
FIG. 5: Alternative examples of PNA molecules tested.

It was observed that, specificity (signal different between KWT and K12S membranes) was very good for all four probes except K13SRC. It was also observed that sensitivity (difference in signal intensity provided by probes K12SRC and K13SRC if compared to K12DAV and K13DAV within the same membrane) was not satisfactory (76-90 vs 44-44) and was difficult to predict and understand based on the sequences shown in FIG. 3.

b) PNA Molecules Containing Alternative Variants at the Abasic or "Blank" Position The specific structures of the probes immobilised on nylon membranes and tested as per FIG. 2, are shown in FIG. 5 below. In this case, the probes were spotted at 50 µM (half the concentration of the 6-neg probes tested in FIG. 4).

In FIG. 5, Glu probes have standard glutamic acid units at both C and N terminal ends. U and Glu correspond to an abasic unit devoid of any substituent at the gamma position. CBU corresponds to an abasic unit comprising a neutral (methyl) group at its gamma position. CBC corresponds to an abasic unit having at its gamma position a moiety containing a carboxylic acid group.

The results of the signals measured for each probe are shown in FIG. 6.

It was observed that CBC probes (in which the unit at the abasic position contains a carboxylic group) exhibited very similar intensities between the four different probes (K12SRC, K12DAV, K13SRC and K13DAV) while keeping an acceptable level of specificity. However, the signal intensities were relatively low.

Figure 7:
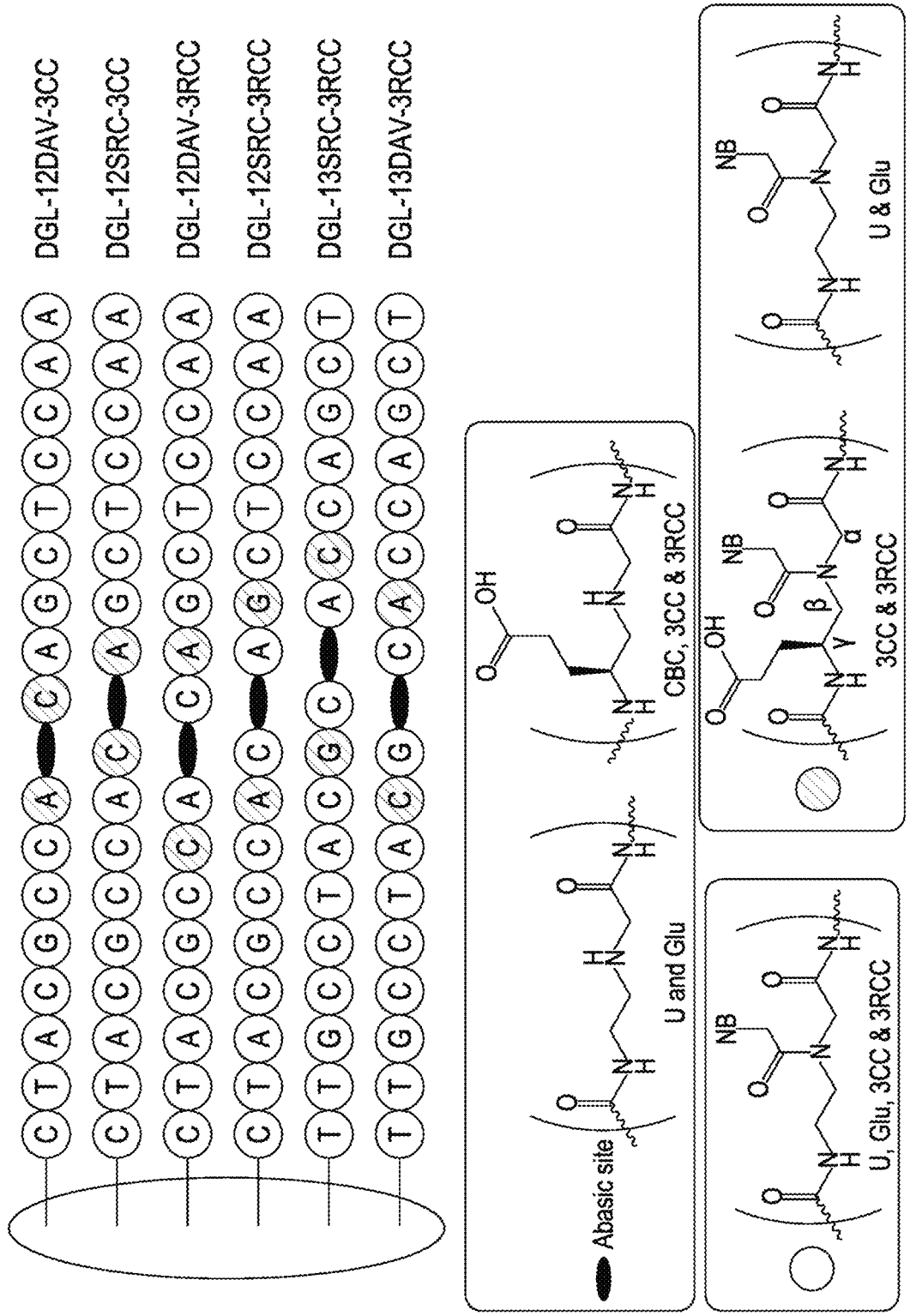
FIG. 7: Alternative examples of PNA molecules tested.

It was also observed that the other probes suffered from high levels of variation in terms of intensity between the 4 types of probes.

c) PNA Molecules Containing Alternative Variants at the Abasic or "Blank" Position, as Well as Variants in Other Units Containing a Nucleobase The specific structures of the probes immobilised on nylon membranes and tested as per FIG. 2, are shown in FIG. 7 below. The probes were spotted at 10, 20 and 50 μM.

Figure 8:
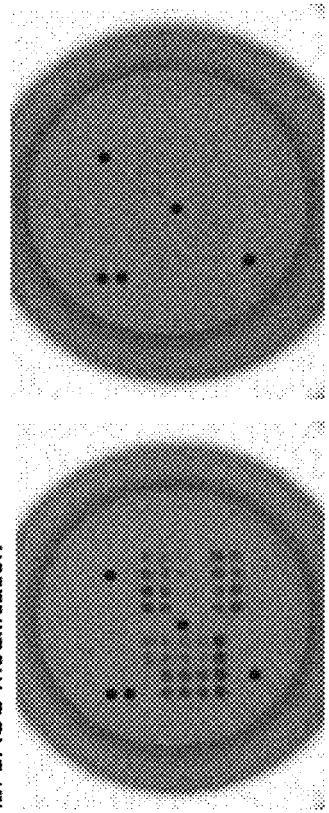
FIG. 8: Results of the intensity measured for the PNA molecules of FIG. 8.

The results of the signals measured for each probe are shown in FIG. 8.

It was observed that 3RCC configuration was the best for PNA K12SRC and K12DAV in terms of specificity (55 vs 3 and 55 vs 5, respectively). In this configuration, the blank position is separated on each side from a nucleobase unit having at its gamma position a moiety containing a carboxylic acid group by a nucleobase unit devoid of any substituent at the gamma position. This configuration also allowed signals to be of similar intensity, unlike the results obtained with 6Neg PNA structures. It was also observed that the probes performed better when the nucleobase units having at their gamma position a moiety containing a carboxylic acid group was not immediately adjacent the abasic chiral unit (3CC probes).

It was also observed that the standard probes (U and Glu probes which only have negative charges through their natural amino acid glutamic groups at both C and N ends) gave lower specificity, since their triggered a higher signal when using the negative control DNA K12S.

Probes K13SRC and K13DAV were then tested with the 3RCC configuration. The probes were spotted at 20 μM. The results are shown in FIG. 9.

It can be seen from FIG. 9 that the 3RCC modifications offered superior performance both in respect of sensitivity and specificity.

d) Use of Bead Support as an Alternative to Membrane

Figure 10:
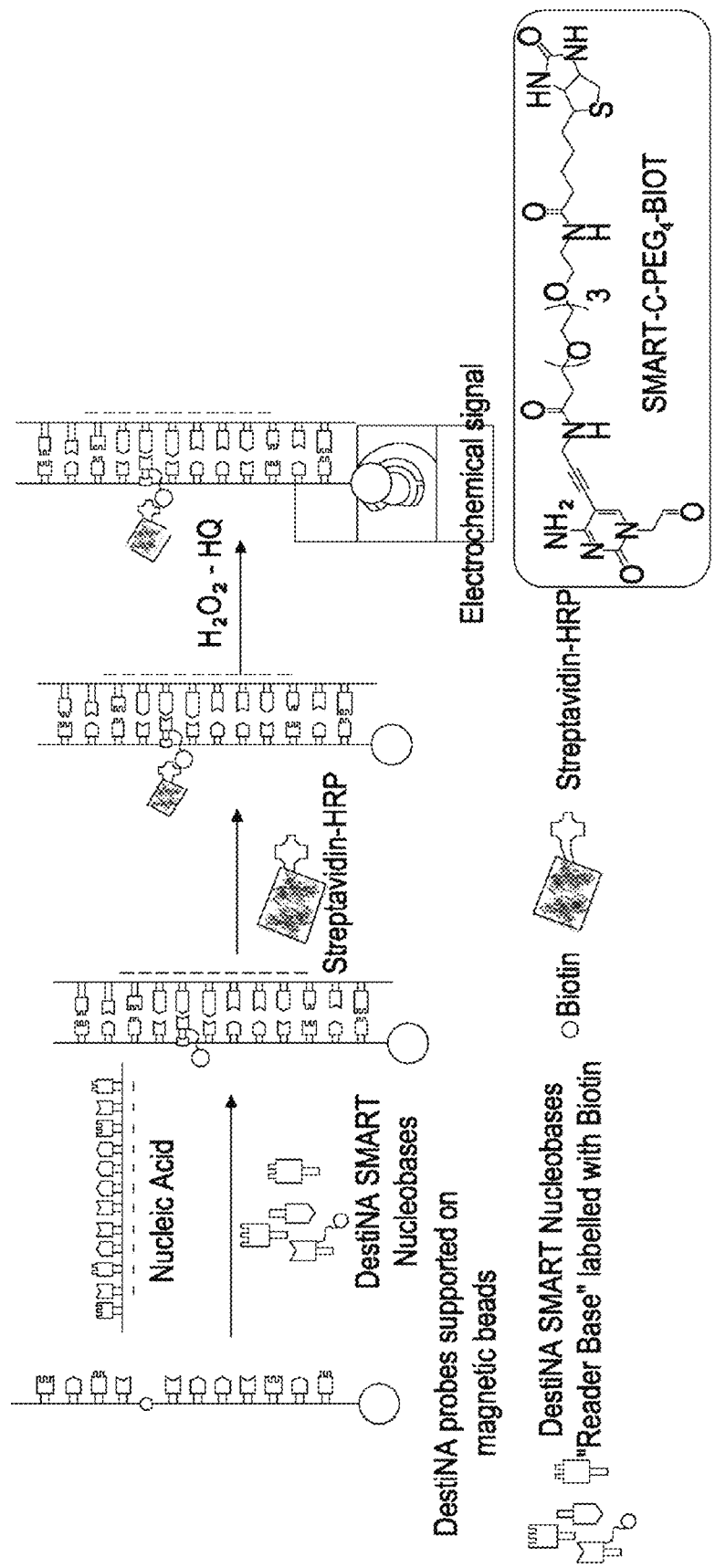
FIG. 10: Examples of PNA molecules tested using a different support.

Probes DGL-13SRC-CBC and DGL-13SRC-3RCC (see FIG. 10 below) were covalently bound to magnetic microspheres instead of nylon membranes and SMART nucleobase incorporation detected via electrochemical detection rather than colorimetry.

Probes were coupled to Dynabeads Carboxylic Acid microspheres (ThermoFisher Scientific, US) using standard carbodiimide coupling chemistry in two steps. The microspheres were washed (×2, 0.02% Tween-20, 200 μL and ×2, 0.1% SDS, 200 μL), resuspended in water (~1 million microspheres per 100 μL) and diluted in 2× saline sodium citrate (SSC) and 0.1% sodium dodecyl sulfate (SDS) with the pH adjusted to 6.0 (buffer A) (100 microspheres per μL). 23.5 μL of Buffer A, 12.5 μL of the functionalised microspheres (dispersed in Buffer A, containing 100 microspheres per μL), 4 μL of SMART-C-PEG-Biotin (500 μM), 7.5 μL of either s-miRNA122 or controls s-miRNA21 and s-mRNA122-A (at 1 μM, 100 nM, 10 nM or 1 nM) and 2.5 μL of reducing agent, sodium cyanoborohydride (20 mM) were added in a 200 μL eppendorf, vortexed and incubated (41° C. for 30 min, thermal cycler). The microspheres were then washed twice with Buffer A, re-suspended (in 50 μL of Buffer A), followed by addition of 10 μL of Streptavidn-HRP for 10 min. Following washing steps (3 min magnetic separation) hydroquinone (HQ) was used as electron transfer mediator and oxygen peroxide ($H_2O_2$) as HRP substrate. At this stage, amperometric measurement using a Screen-printed carbon electrodes (SPCEs) (Dropsens, Spain) was performed.

Figure 11:
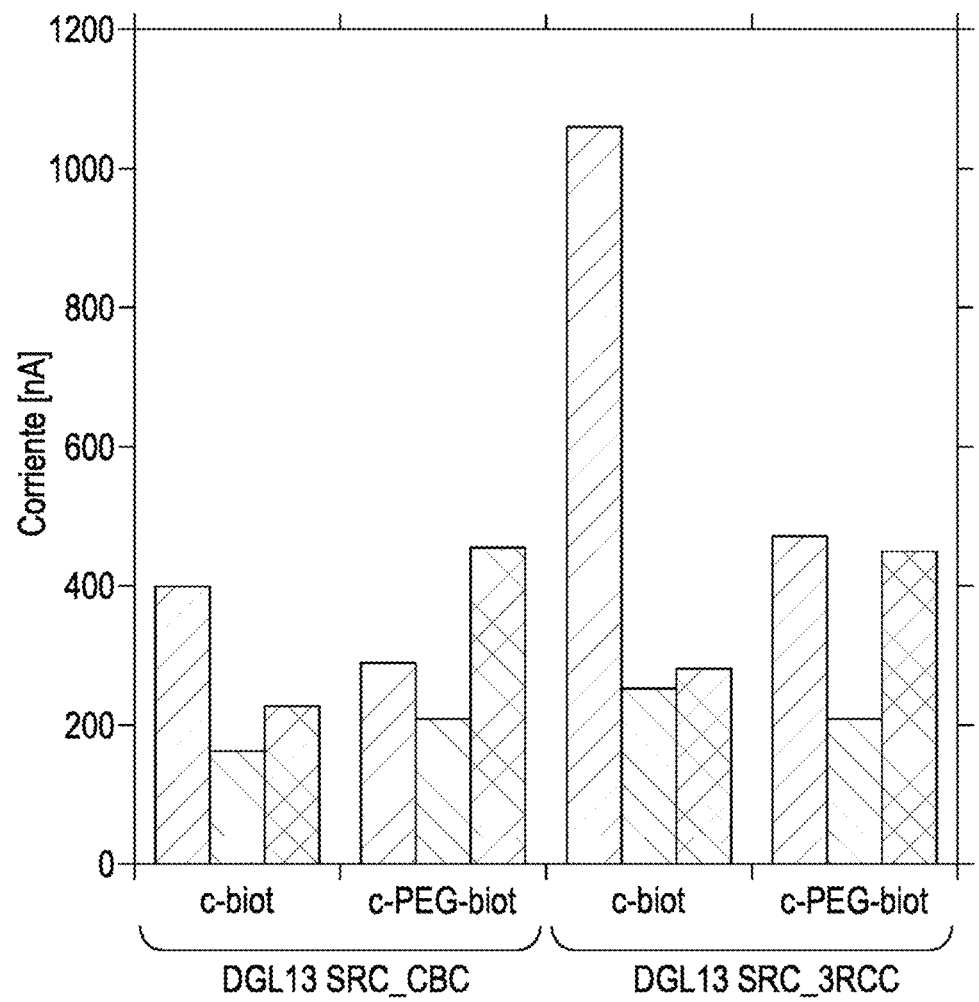
FIG. 11: Results of the intensity measured for the PNA molecules of FIG. 10.

The results are shown in FIG. 11.

It was observed that a DGL-13SRC-3RCC probe (gamma-modified unit at blank position separated on each side from a gamma-modified nucleobase unit having a moiety containing a carboxylic acid group by a nucleobase unit devoid of any substituent at the gamma position) improved 3-fold the specific signal generated, as compared with a DGL-13SRC-3CBC probe (gamma-modified unit at blank position with no gamma-modified nucleobase units).

The above experiments demonstrate the advantages of power of combining chiral modifications both at the abasic unit and different positions in the PNA probe.

While the above tests show superior performance for probes having gamma-modified unit at blank position separated on each side from a gamma-modified nucleobase unit having a moiety containing a carboxylic acid group by a nucleobase unit devoid of any substituent at the gamma position, it will be appreciated that the specific position of the gamma-modified nucleobase units in the probe may be altered without compromising the improved performance of the probe. For example, the gamma-modified nucleobase units may be located two, three or four units away from the blank position. The optimal location of one or more gamma-modified nucleobase units may depend on a number of factors, such as the length of the probe, and the specific application for the probe.

e) Use of Chiral Modified-PNA Probes for Circulating microRNA (miRNA) Detection with a Chemiluminescent Platform (Microplate Reader).

PNA oligomers containing and/or derived from monomers A8 and A9 above, were designed/prepared to allow anti-parallel hybridisation with mature miRNA122 strands (Table 1). As shown in Table 1 (see below), PNA oligomers containing unmodified PNA monomers were synthesised, such as the probes DGL122_3.0-5.0 and some other probes carrying three or more gamma-modified units (DGL122_1.2, 4.1, 4.2).

Figure 12:
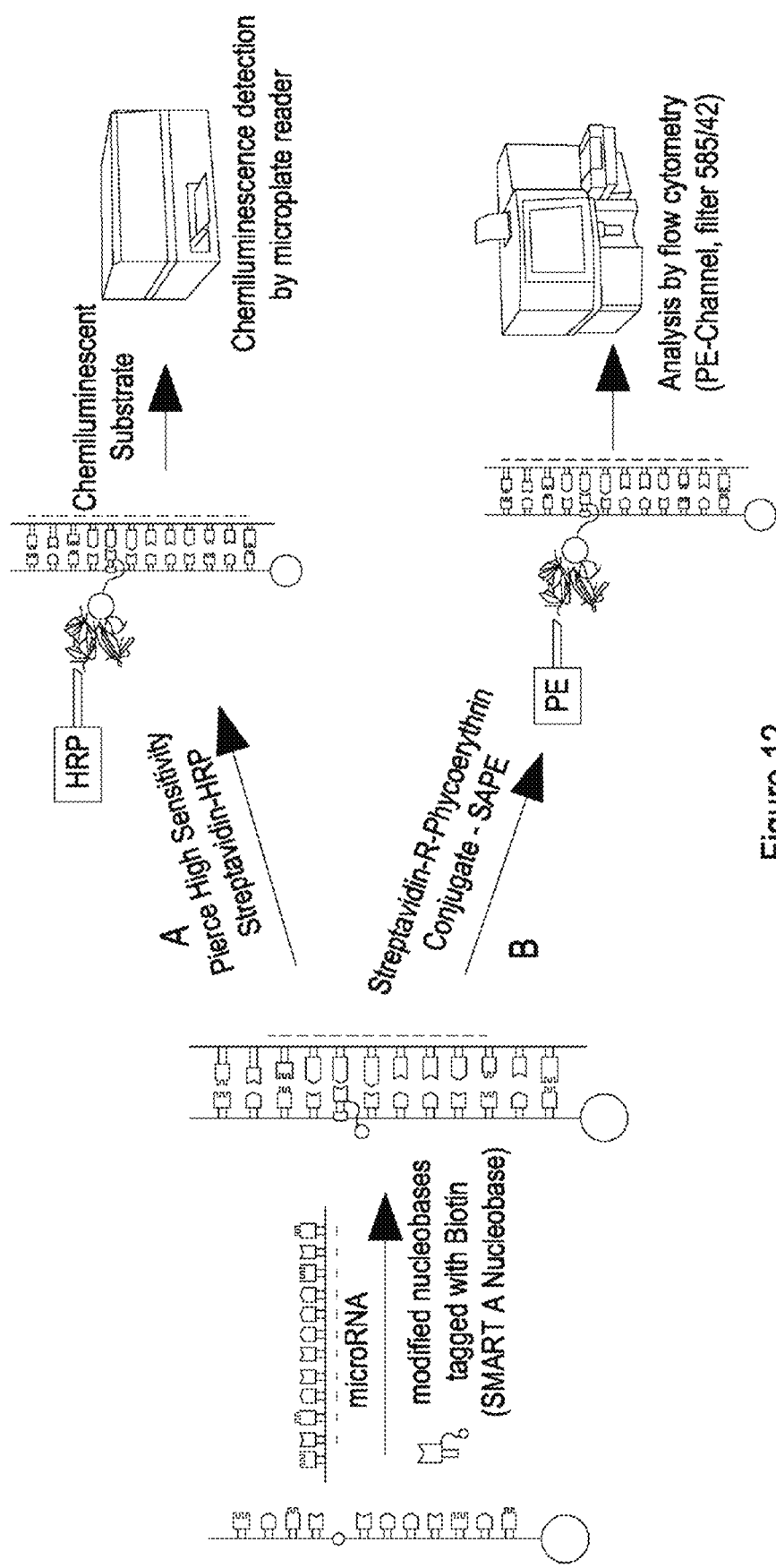
FIG. 12: A scheme representing two alternative methods with which to test PNA probes: A) Chemiluminescent approach (using a microplate reader); B) Fluorometric approach (exploiting flow cytometry).

In order to test the PNA molecules, modified nucleobases tagged with Biotin (SMART-C-Nucleobase-Biotin) were used along with a chemiluminescent method (as shown in the scheme of FIG. 12A).

PNA molecules were tested to assess the specificity and sensitivity of the PNA molecules in relation to: i) the presence of gamma-modified units; ii) the presence of gamma-modifications within the abasic unit; iii) abasic unit position and length of the PNA oligomers (see Table 1 below).

In this method, probes modified at their N-terminal with an amino-pegylated group were covalently bound to carboxylated Dynabeads® (M-270 Carboxylic Acid) using a two-step protocol (without NHS) carbodiimide coupling chemistry according to the manufacturer protocol (Thermo Fisher Scientific).

Figure 13:
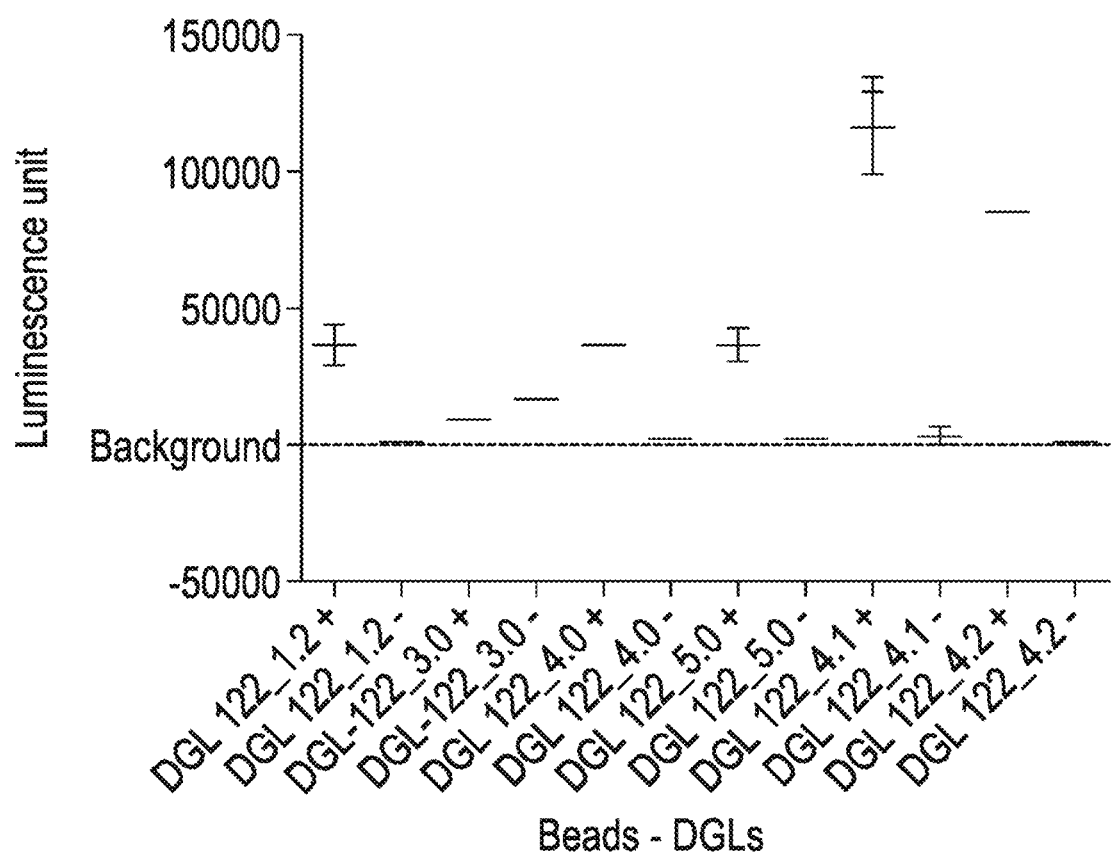
FIG. 13: Performances of the PNA oligomers described in Table 1 (see below). (+) positive signal—oligo 122 (15 nM). (−) negative signal—water as control.

A master mix was prepared with 50 μL of microspheres ($4\times10^4$ beads/uL), SMART-C-Nucleobase-Biotin (Reader Base) (2 μM), nucleic acid strands (Oligo DNA 122) at 15 nM or water instead as control and reducing agent, sodium cyanoborohydride (1 mM) and SCD buffer (2×SSC and 0.1% SDS-pH 6.0) up to a final volume of 50 μL. DestiNA master mix was then vortexed and incubated at 41° C. for 1 h in a thermal cycler. Upon completion of the reaction, the microspheres were washed three times with 200 uL of washing Buffer A (PBS-Tween 0.1%). The microspheres were then pelleted and the supernatant removed and incubated for 5 min at RT with 100 uL of Pierce High Sensitivity Streptavidin-HRP (1:8000) solution (Thermo Fisher Scientific). Following washing steps (4× in Buffer A), the microspheres were pelleted and re-supernatanted in 100 uL of substrate—SuperSignal ELISA Pico Chemiluminescent Substrate (Thermo Fisher Scientific). The microspheres were incubated for 5 min at RT. Upon completion of the incubation, the microspheres/substrate was transferred (100 uL) to the substrate (a white 96-well plate) for final reading using a plate reader with chemiluminescence detection capability (FLUOstar Omega) (FIG. 12A). The results are shown in FIG. 13.

The best performance results were obtained with capture probes 122_1.2, 122_4.1 and 1224.2. Specifically, it was observed that 122_1.2, 1224.1 and 122_4.2 probes with either a gamma-modified unit at the blank position (a gamma modified abasic position) or distributed across the PNA backbone have an improved specific signal generated, as compared with a DGL122_3.0-5.0 probes (without a gamma-modified unit at the blank position or a gamma-modified nucleobase unit across the PNA backbone).

PNA oligomers 122_4.1 (not having a gamma-modified unit at the blank position and two gamma-modified nucleobases on the left side and a single gamma-modified nucleobase on the right side (see Table 1)) exhibited good performance. This shows that the performance of a PNA Oligomer (i.e. an improvement in the signal-to-background ratio; where the background is compared to that obtained when the reaction is carried out using water as control (DestiNA probes followed by "-" in FIG. 13)) is in part dependent on the gamma-modified nucleobase units' position within the probe These results confirm that the optimal location and number of gamma-modified nucleobase units may depend on a number of factors and on the specific application of the probe.

f) Use of Chiral Modified-PNA Probes for Circulating microRNA (miRNA) Detection with Flow Cytometry Flow cytometry was used to further study the effect of gamma-modified units at "blank positions" as well as those distributed across the PNA oligomer's backbone (FIG. 12B).

Three PNA oligomers containing and/or derived from monomers A8 and A9 above, were designed/prepared to allow anti-parallel hybridisation with mature miRNA21 strands (Table 2). PNA oligomers DGL21_2.0 and DGL21_6.0 were designed to hybridize to the same region of mature miRNA21. Both Oligomers carry two gamma-modified units respectively on the two thymine nucleobases beside (or adjacent) the blank position. Additionally, DGL21_6.0 contains a gamma-modified unit at the blank position and the sequence is slightly longer (19-mer instead of 17). The other 17-mer PNA oligomer (DGL21_3.0) was designed to allow anti-parallel hybridisation to a different region of the mature miRNA21 strand and carries two gamma-modified units on the thymine nucleobases either side of the blank position (Table 2). For the three PNA oligomers, the blank position was positioned so that post-hybridisation, the mature miRNA21 strand presents a uracil (Table 2, nucleobases shown in green) in front of the blank position thereby allowing incorporation of an adenine modified nucleobase tagged with Biotin (SMART-A-Nucleobase-Biotin).

PNA oligomers DGL21_2.0, DGL21_6.0 and DGL21_3.0 were covalently bound to Dynabeads Carboxylic Acid microspheres (ThermoFisher Scientific) using standard carbodiimide coupling chemistry in two steps (coupling was performed as reported above). To assess the specificity and sensitivity of the PNA molecules, performance of microspheres was assessed by selective incorporation of SMART-A-Nucleobase-Biotin (Reader Base).

The microspheres were processed using a flow cytometric method. A master mix was prepared with 50 μL of microspheres (8×10$^7$ beads/uL), SMART-A-Nucleobase-Biotin (30 μM), nucleic acid strands (Oligo DNA 21) at 15 nM or water instead as control and reducing agent, sodium cyanoborohydride (150 μM) and Phosphate Buffer pH 6 (150 mM) up to a final volume of 50 μL. The master mix was then vortexed and incubated at 41° C. for 1 h in a thermal cycler. Upon the completion of the reaction, the microspheres were washed three times with 200 uL of washing Buffer A (PBS-Tween 0.1%). The microspheres were then pelleted and the supernatant removed and incubated for 1 h RT with 100 uL of Streptavidin-R-Phycoerythrin Conjugate—SAPE (20 μg/mL), purchased from Thermo Fisher Scientific. After SAPE incubation, microspheres were analysed by BD FACSCanto (PE-Channel, filter 585/42) and dot-plots obtained through Flowjo.

The results are shown in FIG. 14.

Population shifts on the PE channel were clearly seen with microspheres containing the PNA oligomer DGL 21_6.0. It was observed that the DGL 21_6.0 probe (containing the gamma-modified unit at the blank position and others distributed across the PNA backbone) enabled the efficient dynamic incorporation of the Reader Base with a specific signal generated (population shift on the PE channel) (FIG. 14), as compared with a DGL21_2.0 and DGL21_3.0_probes (without gamma-modified unit at the blank position) (FIG. 15). These results show how the adding of gamma-modification at the blank position (DGL 21_6.0) brings a superior SMART-A-Nucleobase-Biotin incorporation when compared to a pretty similar sequence but without gamma-modification at the blank position such as DGL21_2.0 (see Table 2).

The invention claimed is:

1. A PNA oligomer, wherein the PNA oligomer has the general formula:

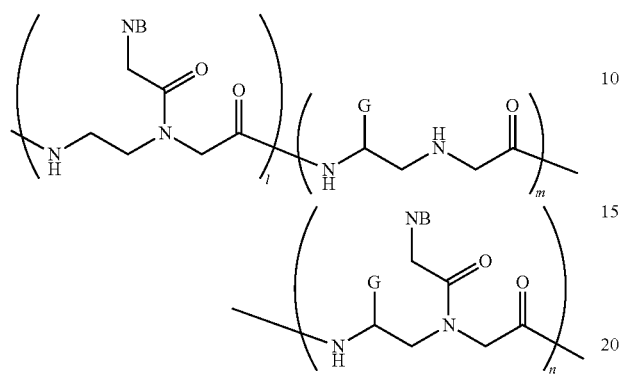

Formula (V)

wherein:

G is a charged moiety, or a moiety capable of carrying a charge at a pH in the range of 6-8;

NB is a nucleobase; and l≥1; m≥1; and n≥0.

2. The PNA oligomer of claim 1, wherein the total number of PNA units (l+m+n) in the oligomer is in the range of 12-24.

3. The PNA oligomer of claim 1, wherein n+m is in the range of 3-5.

4. The PNA oligomer of claim 1 wherein the ratio of the number of units having a "G" moiety in formula (V), to the total number of repeat units, is in the range of 1:10-1:2.

5. The PNA oligomer of claim 1, wherein m=1.

6. The PNA oligomer of claim 1, wherein the PNA molecule is covalently attached to a solid support.

7. The PNA oligomer of claim 1, wherein n≥1.

8. A method for preparing a PNA oligomer according to claim 1, the method comprising reacting one or more PNA monomers so as to form the PNA oligomer, wherein the one or more PNA monomers comprise at its gamma position a charged moiety or a moiety capable of carrying a charge at a predetermined pH, and wherein the one or more PNA monomers each have the general formula:

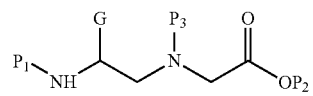

Formula (I)

wherein: G is a charged moiety, or a moiety capable of carrying a charge at a pH in the range of 6-8;

$P_1$ is a protective group P, or is hydrogen;

$P_2$ is a protective group P, or is hydrogen, or is a group selected from the list consisting of alkyl, cycloalkyl, aryl, aralkyl, or halogen, $P_3$ is hydrogen, or is a protective group P, or is a group represented by formula (II) below:

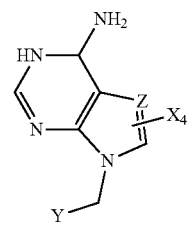

Formula (II)

wherein NB is a nucleobase.

9. A method according to claim 8, the method comprising the preliminary step of covalent bonding a/the PNA monomer on a solid support through its C-terminal.

10. A method of characterising a nucleotide in a nucleic acid sequence, said method comprising the steps of:

wherein Y is a functional group capable of reversible covalent reactions;

$X_1$-$X_4$ is a detectable tag, spacer-tag combination or hydrogen; and

Z is carbon or nitrogen;

wherein the PNA oligomer comprises a moiety capable of reacting reversibly with functional group Y and wherein the modified base which integrates with the nucleic acid/PNA duplex is complementary to that of the nucleotide to be characterised, the nucleotide being characterised by mass spectrometry or by means of the detectable tag of the modified base.

* * * * *

UNITED STATES PATENT AND TRADEMARK OFFICE
CERTIFICATE OF CORRECTION

| | |
|---|---|
| PATENT NO. | : 11,242,526 B2 |
| APPLICATION NO. | : 16/317240 |
| DATED | : February 8, 2022 |
| INVENTOR(S) | : Ilyine et al. |

It is certified that error appears in the above-identified patent and that said Letters Patent is hereby corrected as shown below:

On the Title Page

(30) Foreign Application Priority Data: Please correct "1616556" to read -- 1616556.5 --

(56) References Cited, OTHER PUBLICATIONS, Page 2, Column 2, Line 14: Please correct "Tilanl" to read -- Tilani --

In the Specification

Column 1, Line 26: Please correct "VO" to read -- WO --

Column 25, Line 15: Please correct "1224.2" to read -- 122_4.2 --

Column 25, Line 16: Please correct "1224.1" to read -- 122_4.1 --

In the Claims

Column 50, Lines 27-51: Please delete Claim 10 and replace with the following:
-- A method of characterising a nucleotide in a nucleic acid sequence, said method comprising the steps of:
    (a) contacting a nucleic acid with a peptide nucleic acid (PNA) oligomer according to claim 1, the PNA oligomer being capable of hybridising to a portion of the nucleic acid, to form a nucleic acid/PNA duplex; and
    (b) contacting the nucleic acid/PNA duplex with one or more modified bases selected from the group consisting of:

Signed and Sealed this
Ninth Day of August, 2022

Katherine Kelly Vidal
*Director of the United States Patent and Trademark Office*

(i)
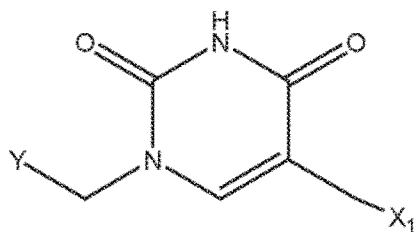
(ii)
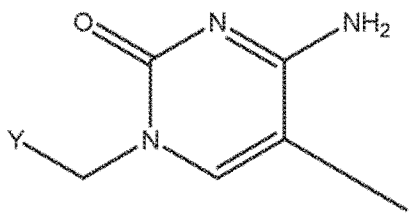
(iii)
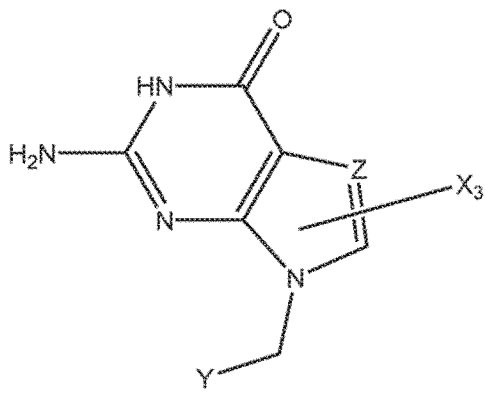
; and
(iv)
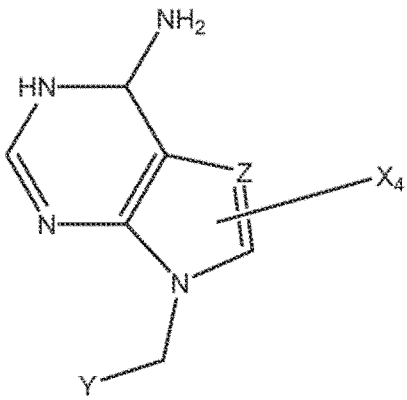
wherein Y is a functional group capable of reversible covalent reactions; $X_1$-$X_4$ is a detectable tag, spacer-tag combination or hydrogen; and Z is carbon or nitrogen;

wherein the PNA oligomer comprises a moiety capable of reacting reversibly with functional group Y and wherein the modified base which integrates with the nucleic acid/PNA duplex is complementary to that of the nucleotide to be characterised, the nucleotide being characterised by mass spectrometry or by means of the detectable tag of the modified base. --

SEQUENCE LISTING

```
<160> NUMBER OF SEQ ID NOS: 27

<210> SEQ ID NO 1
<211> LENGTH: 17
<212> TYPE: DNA
<213> ORGANISM: Artificial Sequence
<220> FEATURE:
<223> OTHER INFORMATION: DGL-12DAV-6neg
<220> FEATURE:
<221> NAME/KEY: modified_base
<222> LOCATION: (2)..(2)
<223> OTHER INFORMATION: Gamma modified thymine
<220> FEATURE:
```

<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (5)..(5)
<223> OTHER INFORMATION: Gamma modified guanine
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (8)..(8)
<223> OTHER INFORMATION: Gamma modified adenine
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: modified_base
<222> LOCATION: (9)..(9)
<223> OTHER INFORMATION: Abasic position
<220> FEATURE:
<221> NAME/KEY: modified_base
<222> LOCATION: (10)..(10)
<223> OTHER INFORMATION: Gamma modified cytosine
<220> FEATURE:
<221> NAME/KEY: modified_base
<222> LOCATION: (13)..(13)
<223> OTHER INFORMATION: Gamma modified cytosine
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (16)..(16)
<223> OTHER INFORMATION: Gamma modified cytosine

<400> SEQUENCE: 1
cnacnccnnn agntnaa                                                    17

<210> SEQ ID NO 2
<211> LENGTH: 18
<212> TYPE: DNA
<213> ORGANISM: Artificial Sequence
<220> FEATURE:
<223> OTHER INFORMATION: DGL-12SRC-6neg
<220> FEATURE:
<221> NAME/KEY: modified_base
<222> LOCATION: (2)..(2)
<223> OTHER INFORMATION: Gamma modified thymine
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (6)..(6)
<223> OTHER INFORMATION: Gamma modified cytosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: Gamma modified cytosine
<220> FEATURE:
<221> NAME/KEY: misc_feature
<222> LOCATION: (9)..(11)
<223> OTHER INFORMATION: n is a, c, g, or t

```
<220> FEATURE:
<221> NAME/KEY: modified_base
<222> LOCATION: (10)..(10)
<223> OTHER INFORMATION: Abasic position
<220> FEATURE:
<221> NAME/KEY: modified_base
<222> LOCATION: (11)..(11)
<223> OTHER INFORMATION: Gamma modified adenine
<220> FEATURE:
<221> NAME/KEY: modified_base
<222> LOCATION: (14)..(14)
<223> OTHER INFORMATION: Gamma modified thymine
<220> FEATURE:
<221> NAME/KEY: modified_base
<222> LOCATION: (17)..(17)
<223> OTHER INFORMATION: Gamma modified adenine
<220> FEATURE:
<221> NAME/KEY: misc_feature
<222> LOCATION: (17)..(17)
<223> OTHER INFORMATION: n is a, c, g, or t

<400> SEQUENCE: 2
cnacgncann ngctccna                                              18

<210> SEQ ID NO 3
<211> LENGTH: 18
<212> TYPE: DNA
<213> ORGANISM: Artificial Sequence
<220> FEATURE:
<223> OTHER INFORMATION: DGL-13SRC-6neg
<220> FEATURE:
<221> NAME/KEY: modified_base
<222> LOCATION: (3)..(3)
<223> OTHER INFORMATION: Gamma modified guanine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (6)..(6)
<223> OTHER INFORMATION: Gamma modified thymine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (10)..(10)
<223> OTHER INFORMATION: Gamma modified cytosine
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: modified_base
<222> LOCATION: (11)..(11)
<223> OTHER INFORMATION: Abasic position
<220> FEATURE:
<221> NAME/KEY: modified_base
<222> LOCATION: (12)..(12)
<223> OTHER INFORMATION: Gamma modified adenine
<220> FEATURE:
<221> NAME/KEY: modified_base
<222> LOCATION: (15)..(15)
<223> OTHER INFORMATION: Gamma modified adenine
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (17)..(17)
<223> OTHER INFORMATION: Gamma modified cytosine
<220> FEATURE:
<221> NAME/KEY: misc_feature
<222> LOCATION: (17)..(17)
```

```
<223> OTHER INFORMATION: n is a, c, g, or t

<400> SEQUENCE: 3
ttnccnacgn nnccngnt                                                 18

<210> SEQ ID NO 4
<211> LENGTH: 18
<212> TYPE: DNA
<213> ORGANISM: Artificial Sequence
<220> FEATURE:
<223> OTHER INFORMATION: DGL-13DAV-6neg
<220> FEATURE:
<221> NAME/KEY: modified_base
<222> LOCATION: (3)..(3)
<223> OTHER INFORMATION: Gamma modified guanine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (6)..(6)
<223> OTHER INFORMATION: Gamma modified thymine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: Gamma modified guanine
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: modified_base
<222> LOCATION: (10)..(10)
<223> OTHER INFORMATION: Abasic position
<220> FEATURE:
<221> NAME/KEY: modified_base
<222> LOCATION: (11)..(11)
<223> OTHER INFORMATION: Gamma modified cytosine
<220> FEATURE:
<221> NAME/KEY: modified_base
<222> LOCATION: (14)..(14)
<223> OTHER INFORMATION: Gamma modified cytosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (17)..(17)
<223> OTHER INFORMATION: Gamma modified cytosine
<220> FEATURE:
<221> NAME/KEY: misc_feature
<222> LOCATION: (17)..(17)
<223> OTHER INFORMATION: n is a, c, g, or t

<400> SEQUENCE: 4
ttnccnacnn nacnagnt                                                 18

<210> SEQ ID NO 5
<211> LENGTH: 22
<212> TYPE: DNA
<213> ORGANISM: Artificial Sequence
<220> FEATURE:
<223> OTHER INFORMATION: KWT DNA

<400> SEQUENCE: 5
ttggagctgg tggcgtaggc aa                                            22
```

```
<210> SEQ ID NO 6
<211> LENGTH: 18
<212> TYPE: DNA
<213> ORGANISM: Artificial Sequence
<220> FEATURE:
<223> OTHER INFORMATION: DNA K125

<400> SEQUENCE: 6
ttggagctag tggcgtag                                                   18

<210> SEQ ID NO 7
<211> LENGTH: 18
<212> TYPE: DNA
<213> ORGANISM: Artificial Sequence
<220> FEATURE:
<223> OTHER INFORMATION: DGL-12DAV
<220> FEATURE:
<221> NAME/KEY: misc_feature
<222> LOCATION: (9)..(9)
<223> OTHER INFORMATION: n is a, c, g, or t

<400> SEQUENCE: 7
ctacgccanc agctccaa                                                   18

<210> SEQ ID NO 8
<211> LENGTH: 18
<212> TYPE: DNA
<213> ORGANISM: Artificial Sequence
<220> FEATURE:
<223> OTHER INFORMATION: DGL-12SRC
<220> FEATURE:
<221> NAME/KEY: modified_base
<222> LOCATION: (10)..(10)
<223> OTHER INFORMATION: Gamma modified abasic position
<220> FEATURE:
<221> NAME/KEY: misc_feature
<222> LOCATION: (10)..(10)
<223> OTHER INFORMATION: n is a, c, g, or t

<400> SEQUENCE: 8
ctacgccacn agctccaa                                                   18

<210> SEQ ID NO 9
<211> LENGTH: 18
<212> TYPE: DNA
<213> ORGANISM: Artificial Sequence
<220> FEATURE:
<223> OTHER INFORMATION: DGL-13SRC
<220> FEATURE:
<221> NAME/KEY: modified_base
<222> LOCATION: (11)..(11)
<223> OTHER INFORMATION: Gamma modified abasic position
<220> FEATURE:
<221> NAME/KEY: misc_feature
<222> LOCATION: (11)..(11)
<223> OTHER INFORMATION: n is a, c, g, or t

<400> SEQUENCE: 9
ttgcctacgc naccagct                                                   18

<210> SEQ ID NO 10
<211> LENGTH: 18
<212> TYPE: DNA
<213> ORGANISM: Artificial Sequence
<220> FEATURE:
<223> OTHER INFORMATION: DGL-13DAV
<220> FEATURE:
<221> NAME/KEY: modified_base
<222> LOCATION: (10)..(10)
<223> OTHER INFORMATION: Gamma modified abasic position
<220> FEATURE:
```

```
<221> NAME/KEY: misc_feature
<222> LOCATION: (10)..(10)
<223> OTHER INFORMATION: n is a, c, g, or t

<400> SEQUENCE: 10
ttgcctacgn caccagct                                                 18

<210> SEQ ID NO 11
<211> LENGTH: 18
<212> TYPE: DNA
<213> ORGANISM: Artificial Sequence
<220> FEATURE:
<223> OTHER INFORMATION: DGL-12DAV-3CC
<220> FEATURE:
<221> NAME/KEY: modified_base
<222> LOCATION: (8)..(8)
<223> OTHER INFORMATION: Gamma modified adenine
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: modified_base
<222> LOCATION: (9)..(9)
<223> OTHER INFORMATION: Gamma modified abasic position
<220> FEATURE:
<221> NAME/KEY: modified_base
<222> LOCATION: (10)..(10)
<223> OTHER INFORMATION: Gamma modified cytosine

<400> SEQUENCE: 11
ctacgccnnn agctccaa                                                 18

<210> SEQ ID NO 12
<211> LENGTH: 18
<212> TYPE: DNA
<213> ORGANISM: Artificial Sequence
<220> FEATURE:
<223> OTHER INFORMATION: DGL-12SRC-3CC
<220> FEATURE:
<221> NAME/KEY: modified_base
<222> LOCATION: (9)..(9)
<223> OTHER INFORMATION: Gamma modified cytosine
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: modified_base
<222> LOCATION: (10)..(10)
<223> OTHER INFORMATION: Gamma modified abasic position
<220> FEATURE:
<221> NAME/KEY: modified_base
<222> LOCATION: (11)..(11)
<223> OTHER INFORMATION: Gamma modified adenine

<400> SEQUENCE: 12
ctacgccann ngctccaa                                                 18

<210> SEQ ID NO 13
<211> LENGTH: 18
<212> TYPE: DNA
<213> ORGANISM: Artificial Sequence
<220> FEATURE:
<223> OTHER INFORMATION: DGL-12DAV-3RCC
<220> FEATURE:
<221> NAME/KEY: modified_base
<222> LOCATION: (7)..(7)
<223> OTHER INFORMATION: Gamma modified cytosine
<220> FEATURE:
<221> NAME/KEY: misc_feature
<222> LOCATION: (7)..(7)
<223> OTHER INFORMATION: n is a, c, g, or t
```

```
<220> FEATURE:
<221> NAME/KEY: modified_base
<222> LOCATION: (9)..(9)
<223> OTHER INFORMATION: Gamma modified abasic position
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: Gamma modified adenine
<220> FEATURE:
<221> NAME/KEY: misc_feature
<222> LOCATION: (11)..(11)
<223> OTHER INFORMATION: n is a, c, g, or t

<400> SEQUENCE: 13
ctacgcnanc ngctccaa                                                   18

<210> SEQ ID NO 14
<211> LENGTH: 18
<212> TYPE: DNA
<213> ORGANISM: Artificial Sequence
<220> FEATURE:
<223> OTHER INFORMATION: DGL-12SRC-3RCC
<220> FEATURE:
<221> NAME/KEY: modified_base
<222> LOCATION: (8)..(8)
<223> OTHER INFORMATION: Gamma modified adenine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (10)..(10)
<223> OTHER INFORMATION: Gamma modified abasic position
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (12)..(12)
<223> OTHER INFORMATION: Gamma modified guanine
<220> FEATURE:
<221> NAME/KEY: misc_feature
<222> LOCATION: (12)..(12)
<223> OTHER INFORMATION: n is a, c, g, or t

<400> SEQUENCE: 14
ctacgccncn anctccaa                                                   18

<210> SEQ ID NO 15
<211> LENGTH: 18
<212> TYPE: DNA
<213> ORGANISM: Artificial Sequence
<220> FEATURE:
<223> OTHER INFORMATION: DGL-13SRC-3RCC
<220> FEATURE:
<221> NAME/KEY: modified_base
<222> LOCATION: (9)..(9)
<223> OTHER INFORMATION: Gamma modified guanine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: Gamma modified abasic position
<220> FEATURE:
<221> NAME/KEY: misc_feature
<222> LOCATION: (11)..(11)
```

<223> OTHER INFORMATION: n is a, c, g, or t
<220> FEATURE:
<221> NAME/KEY: modified_base
<222> LOCATION: (13)..(13)
<223> OTHER INFORMATION: Gamma modified cytosine
<220> FEATURE:
<221> NAME/KEY: misc_feature
<222> LOCATION: (13)..(13)
<223> OTHER INFORMATION: n is a, c, g, or t

<400> SEQUENCE: 15
ttgcctacnc nancagct                                                 18

<210> SEQ ID NO 16
<211> LENGTH: 18
<212> TYPE: DNA
<213> ORGANISM: Artificial Sequence
<220> FEATURE:
<223> OTHER INFORMATION: DGL-13DAV-3RCC
<220> FEATURE:
<221> NAME/KEY: modified_base
<222> LOCATION: (8)..(8)
<223> OTHER INFORMATION: Gamma modified cytosine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (10)..(10)
<223> OTHER INFORMATION: Gamma modified abasic position
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (12)..(12)
<223> OTHER INFORMATION: Gamma modified adenine
<220> FEATURE:
<221> NAME/KEY: misc_feature
<222> LOCATION: (12)..(12)
<223> OTHER INFORMATION: n is a, c, g, or t

<400> SEQUENCE: 16
ttgcctangn cnccagct                                                 18

<210> SEQ ID NO 17
<211> LENGTH: 22
<212> TYPE: RNA
<213> ORGANISM: Homo sapiens

<400> SEQUENCE: 17
uggaguguga caauggguguu ug                                           22

<210> SEQ ID NO 18
<211> LENGTH: 18
<212> TYPE: DNA
<213> ORGANISM: Artificial Sequence
<220> FEATURE:
<223> OTHER INFORMATION: DGL122_1.2
<220> FEATURE:
<221> NAME/KEY: modified_base
<222> LOCATION: (3)..(3)
<223> OTHER INFORMATION: gamma modified cytosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: gamma modified cytosine

```
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: modified_base
<222> LOCATION: (6)..(6)
<223> OTHER INFORMATION: Abasic position
<220> FEATURE:
<221> NAME/KEY: modified_base
<222> LOCATION: (8)..(8)
<223> OTHER INFORMATION: gamma modified thymine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (11)..(11)
<223> OTHER INFORMATION: gamma modified thymine
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (14)..(14)
<223> OTHER INFORMATION: gamma modified cytosine
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (16)..(16)
<223> OTHER INFORMATION: gamma modified cytosine
<220> FEATURE:
<221> NAME/KEY: misc_feature
<222> LOCATION: (16)..(16)
<223> OTHER INFORMATION: n is a, c, g, or t

<400> SEQUENCE: 18
aanannantg ncanantc                                                 18

<210> SEQ ID NO 19
<211> LENGTH: 17
<212> TYPE: DNA
<213> ORGANISM: Artificial Sequence
<220> FEATURE:
<223> OTHER INFORMATION: DGL122_3.0
<220> FEATURE:
<221> NAME/KEY: modified_base
<222> LOCATION: (7)..(7)
<223> OTHER INFORMATION: Abasic position
<220> FEATURE:
<221> NAME/KEY: misc_feature
<222> LOCATION: (7)..(7)
<223> OTHER INFORMATION: n is a, c, g, or t

<400> SEQUENCE: 19
caaacancat tgtcaca                                                  17

<210> SEQ ID NO 20
<211> LENGTH: 17
<212> TYPE: DNA
<213> ORGANISM: Artificial Sequence
<220> FEATURE:
<223> OTHER INFORMATION: DGL122_5.0
<220> FEATURE:
<221> NAME/KEY: modified_base
<222> LOCATION: (11)..(11)
<223> OTHER INFORMATION: Abasic position
<220> FEATURE:
<221> NAME/KEY: misc_feature
<222> LOCATION: (11)..(11)
```

```
<223> OTHER INFORMATION: n is a, c, g, or t

<400> SEQUENCE: 20
accattgtca nactcca                                                    17

<210> SEQ ID NO 21
<211> LENGTH: 18
<212> TYPE: DNA
<213> ORGANISM: Artificial Sequence
<220> FEATURE:
<223> OTHER INFORMATION: DGL122_4.0
<220> FEATURE:
<221> NAME/KEY: modified_base
<222> LOCATION: (10)..(10)
<223> OTHER INFORMATION: Abasic position
<220> FEATURE:
<221> NAME/KEY: misc_feature
<222> LOCATION: (10)..(10)
<223> OTHER INFORMATION: n is a, c, g, or t

<400> SEQUENCE: 21
caccattgtn acactcca                                                   18

<210> SEQ ID NO 22
<211> LENGTH: 18
<212> TYPE: DNA
<213> ORGANISM: Artificial Sequence
<220> FEATURE:
<223> OTHER INFORMATION: DGL122_4.1
<220> FEATURE:
<221> NAME/KEY: modified_base
<222> LOCATION: (6)..(6)
<223> OTHER INFORMATION: Gamma modified thymine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: Gamma modified thymine
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: Abasic position
<220> FEATURE:
<221> NAME/KEY: modified_base
<222> LOCATION: (15)..(15)
<223> OTHER INFORMATION: Gamma modified thymine
<220> FEATURE:
<221> NAME/KEY: misc_feature
<222> LOCATION: (15)..(15)
<223> OTHER INFORMATION: n is a, c, g, or t

<400> SEQUENCE: 22
caccantgnn acacncca                                                   18

<210> SEQ ID NO 23
<211> LENGTH: 18
<212> TYPE: DNA
<213> ORGANISM: Artificial Sequence
<220> FEATURE:
<223> OTHER INFORMATION: DGL122_4.2
<220> FEATURE:
<221> NAME/KEY: modified_base
<222> LOCATION: (6)..(6)
<223> OTHER INFORMATION: Gamma modified thymine
<220> FEATURE:
<221> NAME/KEY: misc_feature
```

```
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: Gamma modified thymine
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: modified_base
<222> LOCATION: (10)..(10)
<223> OTHER INFORMATION: Gamma modified abasic position
<220> FEATURE:
<221> NAME/KEY: modified_base
<222> LOCATION: (15)..(15)
<223> OTHER INFORMATION: Gamma modified thymine
<220> FEATURE:
<221> NAME/KEY: misc_feature
<222> LOCATION: (15)..(15)
<223> OTHER INFORMATION: n is a, c, g, or t

<400> SEQUENCE: 23
caccantgnn acacncca                                                   18

<210> SEQ ID NO 24
<211> LENGTH: 19
<212> TYPE: DNA
<213> ORGANISM: Artificial Sequence
<220> FEATURE:
<223> OTHER INFORMATION: DGL21_2.0
<220> FEATURE:
<221> NAME/KEY: modified_base
<222> LOCATION: (7)..(7)
<223> OTHER INFORMATION: Gamma modified thymine
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: Abasic position
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: Gamma modified thymine
<220> FEATURE:
<221> NAME/KEY: misc_feature
<222> LOCATION: (11)..(11)
<223> OTHER INFORMATION: n is a, c, g, or t

<400> SEQUENCE: 24
tcaacancng nctcagata                                                  19

<210> SEQ ID NO 25
<211> LENGTH: 17
<212> TYPE: DNA
<213> ORGANISM: Artificial Sequence
<220> FEATURE:
<223> OTHER INFORMATION: DGL21_3.0
<220> FEATURE:
<221> NAME/KEY: modified_base
<222> LOCATION: (8)..(8)
<223> OTHER INFORMATION: Gamma modified thymine
<220> FEATURE:
<221> NAME/KEY: misc_feature
<222> LOCATION: (8)..(8)
<223> OTHER INFORMATION: n is a, c, g, or t
<220> FEATURE:
```

```
<221> NAME/KEY: modified_base
<222> LOCATION: (10)..(10)
<223> OTHER INFORMATION: Abasic position
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (15)..(15)
<223> OTHER INFORMATION: Gamma modified cytosine
<220> FEATURE:
<221> NAME/KEY: misc_feature
<222> LOCATION: (15)..(15)
<223> OTHER INFORMATION: n is a, c, g, or t

<400> SEQUENCE: 25
atcagtcngn taagnta                                                      17

<210> SEQ ID NO 26
<211> LENGTH: 19
<212> TYPE: DNA
<213> ORGANISM: Artificial Sequence
<220> FEATURE:
<223> OTHER INFORMATION: DGL21_6.0
<220> FEATURE:
<221> NAME/KEY: modified_base
<222> LOCATION: (6)..(6)
<223> OTHER INFORMATION: Gamma modified thymine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: Gamma modified abasic position
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (10)..(10)
<223> OTHER INFORMATION: Gamma modified thymine
<220> FEATURE:
<221> NAME/KEY: misc_feature
<222> LOCATION: (10)..(10)
<223> OTHER INFORMATION: n is a, c, g, or t

<400> SEQUENCE: 26
caacancngn ctgataagc                                                    19

<210> SEQ ID NO 27
<211> LENGTH: 22
<212> TYPE: RNA
<213> ORGANISM: Homo sapiens

<400> SEQUENCE: 27
uagcuuauca gacugauguu ga                                                22
```